US010206739B2

(12) United States Patent
Godara et al.

(10) Patent No.: US 10,206,739 B2
(45) Date of Patent: Feb. 19, 2019

(54) ELECTROSURGICAL DEVICE AND METHODS

(75) Inventors: Neil Godara, Mississauga (CA); Taylor Hillier, Georgetown (CA)

(73) Assignee: Avent, Inc., Alpharetta, GA (US)

(*) Notice: Subject to any disclaimer, the term of this patent is extended or adjusted under 35 U.S.C. 154(b) by 1747 days.

(21) Appl. No.: 11/457,697

(22) Filed: Jul. 14, 2006

(65) Prior Publication Data
US 2007/0027449 A1    Feb. 1, 2007

Related U.S. Application Data

(63) Continuation-in-part of application No. 11/105,527, filed on Apr. 14, 2005, now Pat. No. 8,882,755, and
(Continued)

(51) Int. Cl.
*A61B 18/18*        (2006.01)
*A61B 18/14*        (2006.01)
(Continued)

(52) U.S. Cl.
CPC ...... *A61B 18/1482* (2013.01); *A61B 2018/00023* (2013.01); *A61B 2018/0044* (2013.01);
(Continued)

(58) Field of Classification Search
CPC ...... A61B 18/1482; A61B 2018/00023; A61B 2018/00083; A61B 2018/00791;
(Continued)

(56) References Cited

U.S. PATENT DOCUMENTS

| 4,041,931 A | 8/1977 | Elliott et al. |
| 4,202,349 A | 5/1980 | Jones |

(Continued)

FOREIGN PATENT DOCUMENTS

| CA | 1160932 | 1/1984 |
| EP | 0547772 | 6/1993 |

(Continued)

OTHER PUBLICATIONS

Valleylab—RF Pain Management System, Sep. 16, 2004, http://www.valleylab.com/static/pain/products-generator.html.

*Primary Examiner* — Ahmed Farah
(74) *Attorney, Agent, or Firm* — Dority & Manning, P.A.

(57) ABSTRACT

A method and apparatus are disclosed for delivering energy substantially distal to an electrosurgical device. Embodiments of a device of the present invention may comprise an elongate member having one or more electrically insulated portions and a distal face comprising one or more electrically exposed conductive portions for delivering energy substantially distal to the elongate member. At least one of the one or more electrically insulated portions may extend from a proximal region of the elongate member to a distal end of the elongate member. In addition, a method is provided for creating a lesion at a target site within a body of a human or animal using an electrosurgical device. The method may comprise the steps of: inserting the electrosurgical device into the body such that the electrosurgical device is generally upstanding relative to the target site; and delivering energy from an energy source through a distal face of the electrosurgical device such that the energy is directed substantially distal to the distal face towards the target site.

11 Claims, 17 Drawing Sheets

Related U.S. Application Data a continuation-in-part of application No. 11/105,490, filed on Apr. 14, 2005, now abandoned, and a continuation-in-part of application No. 11/105,524, filed on Apr. 14, 2005, now Pat. No. 7,294,127, said application No. 11/105,527 is a continuation-in-part of application No. 10/087,856, filed on Mar. 5, 2002, now Pat. No. 6,896,675, said application No. 11/105,490 is a continuation-in-part of application No. 10/087,856, filed on Mar. 5, 2002, now Pat. No. 6,896,675, said application No. 11/105,524 is a continuation-in-part of application No. 10/087,856, filed on Mar. 5, 2002, now Pat. No. 6,896,675, application No. 11/457,697, which is a continuation-in-part of application No. 11/381,783, filed on May 5, 2006, now abandoned, and a continuation-in-part of application No. 10/864,410, filed on Jun. 10, 2004, now Pat. No. 7,163,536, and a continuation-in-part of application No. 11/207,707, filed on Aug. 22, 2005, now abandoned, which is a continuation-in-part of application No. 11/079,318, filed on Mar. 15, 2005, now Pat. No. 7,593,778, which is a continuation-in-part of application No. 10/382,836, filed on Mar. 7, 2003, now abandoned, said application No. 11/207,707 is a continuation-in-part of application No. 11/125,247, filed on May 10, 2005, now Pat. No. 7,306,596, which is a continuation-in-part of application No. 10/853,126, filed on May 26, 2004, now abandoned.

(60) Provisional application No. 60/743,511, filed on Mar. 16, 2006, provisional application No. 60/595,559, filed on Jul. 14, 2005, provisional application No. 60/595,560, filed on Jul. 14, 2005, provisional application No. 60/604,348, filed on Aug. 25, 2004.

(51) Int. Cl.
 *A61B 18/00* (2006.01)
 *A61B 90/00* (2016.01)

(52) U.S. Cl.
 CPC ........ *A61B 2018/00083* (2013.01); *A61B 2018/00196* (2013.01); *A61B 2018/00434* (2013.01); *A61B 2018/00791* (2013.01); *A61B 2018/1497* (2013.01); *A61B 2090/064* (2016.02); *A61B 2218/002* (2013.01); *A61B 2218/007* (2013.01)

(58) Field of Classification Search
 CPC . A61B 2018/1497; A61B 18/04; A61B 18/08; A61B 18/082; A61B 18/12; A61B 18/14; A61B 2018/1405; A61B 2018/142; A61B 2018/00071; A61B 2018/00077; A61B 2018/00089; A61B 2018/00178; A61B 2018/00434; A61B 2018/0044; A61B 2018/00797; A61B 2018/00815; A61B 2018/00821
 USPC ............... 606/20–50; 607/96, 98, 102–106; 600/549
 See application file for complete search history.

(56) References Cited

U.S. PATENT DOCUMENTS

| | | |
|---|---|---|
| 4,257,429 A | 3/1981 | Dickhudt et al. |
| 4,419,095 A | 12/1983 | Nebergall et al. |
| 4,447,239 A | 5/1984 | Krutten |
| 4,548,027 A | 10/1985 | Reimels |
| 4,612,934 A | 9/1986 | Borkan |
| 4,657,024 A | 4/1987 | Coneys |
| 5,191,900 A | 3/1993 | Mishra |
| 5,209,749 A | 5/1993 | Buelna |
| 5,342,343 A | 8/1994 | Kitaoka et al. |
| 5,342,357 A | 8/1994 | Nardella |
| 5,397,338 A | 3/1995 | Grey et al. |
| 5,423,807 A * | 6/1995 | Milder ............ 606/20 |
| 5,429,597 A | 7/1995 | DeMello et al. |
| 5,429,617 A | 7/1995 | Hammersmark et al. |
| 5,433,739 A | 7/1995 | Sluijter et al. |
| 5,545,193 A | 8/1996 | Fleischman et al. |
| 5,571,147 A | 11/1996 | Sluijter et al. |
| 5,688,267 A * | 11/1997 | Panescu et al. ........ 606/41 |
| 5,693,043 A | 12/1997 | Kittrell et al. |
| 5,759,174 A | 6/1998 | Fischell et al. |
| 5,766,171 A | 6/1998 | Silvestrini |
| 5,776,092 A | 7/1998 | Farin et al. |
| 5,779,642 A | 7/1998 | Nightengale |
| 5,800,428 A | 9/1998 | Nelson et al. |
| 5,855,577 A | 1/1999 | Murphy-Chutorian et al. |
| 5,895,386 A | 4/1999 | Odell |
| 5,951,546 A | 9/1999 | Lorentzen |
| 6,002,964 A | 12/1999 | Feler et al. |
| 6,056,743 A | 5/2000 | Ellis et al. |
| 6,102,886 A | 8/2000 | Lundquist et al. |
| 6,104,957 A | 8/2000 | Alo et al. |
| 6,112,123 A * | 8/2000 | Kelleher et al. ........ 607/98 |
| 6,126,654 A | 10/2000 | Giba et al. |
| 6,129,726 A | 10/2000 | Edwards |
| 6,146,380 A | 11/2000 | Racz et al. |
| 6,176,857 B1 | 1/2001 | Ashley |
| 6,235,000 B1 | 5/2001 | Milo et al. |
| 6,251,104 B1 | 6/2001 | Kesten et al. |
| 6,277,112 B1 | 8/2001 | Underwood et al. |
| 6,280,441 B1 | 8/2001 | Ryan |
| 6,306,132 B1 | 10/2001 | Moorman et al. |
| 6,315,790 B1 | 11/2001 | Gerberding et al. |
| 6,355,033 B1 | 3/2002 | Moorman et al. |
| 6,379,349 B1 | 4/2002 | Müller et al. |
| 6,464,723 B1 | 10/2002 | Callol |
| 6,471,700 B1 | 10/2002 | Burbank et al. |
| 6,478,793 B1 | 11/2002 | Moorehead |
| 6,501,992 B1 | 12/2002 | Belden et al. |
| 6,562,033 B2 | 5/2003 | Shah et al. |
| 6,575,969 B1 * | 6/2003 | Rittman et al. ........ 606/41 |
| 6,582,426 B2 | 6/2003 | Moorman et al. |
| 6,620,156 B1 | 9/2003 | Garito |
| 6,622,731 B2 | 9/2003 | Daniel et al. |
| 6,726,684 B1 | 4/2004 | Woloszko |
| 6,735,474 B1 | 5/2004 | Loeb et al. |
| 6,757,565 B2 | 6/2004 | Sharkey |
| 6,770,070 B1 | 8/2004 | Balbierz |
| 6,773,446 B1 | 8/2004 | Dwyer et al. |
| 6,780,181 B2 | 8/2004 | Kroll et al. |
| 6,847,849 B2 | 1/2005 | Mamo et al. |
| 6,893,421 B1 | 5/2005 | Larsen et al. |
| 6,902,526 B2 | 6/2005 | Katzman |
| 6,932,811 B2 | 8/2005 | Hooven |
| 6,966,902 B2 | 11/2005 | Tsugita et al. |
| 6,974,454 B2 | 12/2005 | Hooven |
| 7,097,641 B1 | 8/2006 | Arless et al. |
| 7,175,631 B2 | 2/2007 | Wilson et al. |
| 7,306,596 B2 * | 12/2007 | Hillier ........ A61B 18/1477 128/898 |
| 7,462,178 B2 | 12/2008 | Woloszko et al. |
| 8,475,448 B2 * | 7/2013 | Sharareh et al. ........ 606/41 |
| 9,173,700 B2 * | 11/2015 | Godara ........ A61B 18/148 |
| 9,364,281 B2 * | 6/2016 | Lefler ........ A61B 18/1482 |
| 9,820,808 B2 * | 11/2017 | Lefler ........ A61B 18/1482 |
| 2001/0000041 A1 | 3/2001 | Selmon et al. |
| 2001/0027309 A1 | 10/2001 | Elsberry |
| 2001/0056280 A1 | 12/2001 | Underwood |
| 2002/0026127 A1 | 2/2002 | Balbierz |
| 2002/0032440 A1 | 3/2002 | Hooven |
| 2002/0049437 A1 | 4/2002 | Silvestrini |
| 2002/0072739 A1 | 6/2002 | Lee |
| 2002/0091384 A1 | 7/2002 | Godinho de Queiroz e Melo |

(56) References Cited

U.S. PATENT DOCUMENTS

| | | |
|---|---|---|
| 2002/0103484 A1 | 8/2002 | Hooven |
| 2002/0120260 A1 | 8/2002 | Morris et al. |
| 2002/0147485 A1 | 10/2002 | Mamo et al. |
| 2002/0193781 A1 | 12/2002 | Loeb |
| 2003/0014047 A1 | 1/2003 | Woloszko |
| 2003/0015707 A1 | 1/2003 | Bosco |
| 2003/0023239 A1 | 1/2003 | Burbank et al. |
| 2003/0032936 A1 | 2/2003 | Lederman |
| 2003/0040742 A1 | 2/2003 | Underwood |
| 2003/0093007 A1 | 5/2003 | Wood |
| 2003/0100895 A1 | 5/2003 | Simpson et al. |
| 2003/0109870 A1 | 6/2003 | Lee |
| 2003/0125729 A1 | 7/2003 | Hooven |
| 2003/0153906 A1 | 8/2003 | Sharkey |
| 2003/0158545 A1 | 8/2003 | Hovda et al. |
| 2003/0171744 A1 * | 9/2003 | Leung ............ A61B 18/148 606/41 |
| 2003/0212394 A1 | 11/2003 | Pearson et al. |
| 2003/0212395 A1 | 11/2003 | Woloszko |
| 2003/0233125 A1 | 12/2003 | Kaplan et al. |
| 2004/0054366 A1 | 3/2004 | Davidson et al. |
| 2004/0082942 A1 | 4/2004 | Katzman |
| 2004/0106891 A1 | 6/2004 | Langan et al. |
| 2004/0187875 A1 | 9/2004 | He et al. |
| 2004/0199161 A1 | 10/2004 | Truckai et al. |
| 2004/0215287 A1 | 10/2004 | Swoyer et al. |
| 2004/0249373 A1 | 12/2004 | Gronemeyer et al. |
| 2004/0267203 A1 | 12/2004 | Potter et al. |
| 2004/0267254 A1 | 12/2004 | Manzo et al. |
| 2005/0033372 A1 | 2/2005 | Gerber et al. |
| 2005/0049570 A1 | 3/2005 | Chin et al. |
| 2005/0085806 A1 | 4/2005 | Auge II et al. |
| 2005/0096718 A1 | 5/2005 | Gerber et al. |
| 2005/0177209 A1 | 8/2005 | Leung et al. |
| 2005/0177211 A1 | 8/2005 | Leung et al. |
| 2005/0187542 A1 | 8/2005 | Auge |
| 2005/0240238 A1 | 10/2005 | Mamo |
| 2006/0020297 A1 | 1/2006 | Gerber et al. |
| 2006/0025763 A1 | 2/2006 | Nelson et al. |

FOREIGN PATENT DOCUMENTS

| | | |
|---|---|---|
| EP | 0642800 | 3/1995 |
| EP | 0651661 | 6/2000 |
| EP | 0865768 | 2/2003 |
| EP | 1344497 | 9/2003 |
| WO | WO 81/03272 | 11/1981 |
| WO | WO 94/002077 | 2/1994 |
| WO | WO 94/009560 | 4/1994 |
| WO | WO 94/022384 | 10/1994 |
| WO | WO 94/024948 | 11/1994 |
| WO | WO 95/010318 | 4/1995 |
| WO | WO 95/010320 | 4/1995 |
| WO | WO 95/010327 | 4/1995 |
| WO | WO 95/021578 | 8/1995 |
| WO | WO 96/039967 | 12/1996 |
| WO | WO 97/006739 | 2/1997 |
| WO | WO 97/006855 | 2/1997 |
| WO | WO 97/024074 | 7/1997 |
| WO | WO 98/19613 | 5/1998 |
| WO | WO 98/027879 | 7/1998 |
| WO | WO 98/031290 | 7/1998 |
| WO | WO 98/058747 | 12/1998 |
| WO | WO 99/042037 | 8/1999 |
| WO | WO 1999/043263 | 9/1999 |
| WO | WO 1999/048548 | 9/1999 |
| WO | WO 2001/045579 | 6/2001 |
| WO | WO 2001/067975 | 9/2001 |
| WO | WO 2001/070114 | 9/2001 |
| WO | WO 2001/074251 | 10/2001 |
| WO | WO 2001/080724 | 11/2001 |
| WO | WO 2002/045609 | 6/2002 |
| WO | WO 2003/037162 | 5/2003 |
| WO | WO 2003/065917 | 8/2003 |
| WO | WO 2003/103522 | 12/2003 |

* cited by examiner

Prior Art

ELECTROSURGICAL DEVICE AND METHODS

CROSS REFERENCES TO RELATED APPLICATIONS

This application is a continuation-in-part of U.S. patent application Ser. No. 11/105,527 (filed on Apr. 14, 2005), Ser. No. 11/105,490 (filed on Apr. 14, 2005), and Ser. No. 11/105,524 (filed on Apr. 14, 2005), all of which claim the benefit of U.S. Provisional Patent Application 60/604,348 (filed on Aug. 25, 2004), and are continuations-in-part of U.S. patent application Ser. No. 10/087,856 (filed on Mar. 5, 2002), now U.S. Pat. No. 6,896,675. This application is also a continuation-in-part of U.S. patent application Ser. No. 11/381,783 (filed on May 5, 2006). This application is also a continuation-in-part of U.S. patent application Ser. No. 10/864,410 (filed on Jun. 10, 2004). This application is also a continuation-in-part of U.S. patent application Ser. No. 11/207,707 (filed on Aug. 22, 2005). U.S. patent application Ser. No. 11/207,707 is a continuation-in-part of U.S. patent application Ser. No. 11/079,318 (filed on Mar. 15, 2005) which is a continuation-in-part of U.S. patent application Ser. No. 10/382,836 (filed on Mar. 7, 2003). U.S. patent application Ser. No. 11/207,707 is also a continuation-in-part of U.S. patent application Ser. No. 11/125,247 (filed on May 10, 2005), which is a continuation-in-part of Ser. No. 10/853,126 (filed on May 26, 2004). This application also claims the benefit of U.S. Provisional Patent Application 60/743,511 (filed on Mar. 16, 2006), 60/595,559 (filed on Jul. 14, 2005), 60/595,560 (filed on Jul. 14, 2005), and 60/744,518 (filed on Apr. 10, 2006). All of the aforementioned patents and applications are incorporated herein by reference, in their entirety.

TECHNICAL FIELD

The invention relates to electrosurgical devices and methods for the treatment of pain.

BACKGROUND OF THE ART

Electrosurgical procedures typically rely on the application of high frequency, for example radiofrequency (RF), energy to treat, cut, ablate or coagulate tissue structures such as, for example, neural tissue. The high frequency energy is often delivered to a region of tissue from an energy source such as a generator via an active electrode of a probe that is inserted into a patient's body. The resistance of tissue, located proximate the active electrode of the probe, to the high frequency energy, causes the tissue temperature to rise. If the temperature is increased past a certain tissue-dependent level, referred to as the lesioning temperature, tissue damage will occur, and a lesion will form. Often, the tissue proximate to the probe heats up faster than tissue farther away from the probe, which may limit the size of the lesion.

In addition to limited lesion size, prior art devices typically form lesions with minimal extension distal to the tip of the electrode, as described by Bogduk et al. (Neurosurgery, 20(4):529-535, 1987) and as shown in FIG. 16 (FIG. 4 of the Bogduk article). Prior art devices typically include an electrically exposed conductive portion along the length of the device. Bogduk et al. suggest that failures of such prior art devices to effectively lesion target tissue was due to the fact that lesions created by those devices do not extend distal to the distal tip of the devices but rather extend primarily circumferentially to the distal tip, along the length of the exposed conductive portions. Bogduk et al. proceed to suggest that probe electrodes should be positioned such that they run parallel to the target nerve for optimal efficacy.

Scientific literature published since Bogduk et al's study continue to emphasize the importance of positioning the electrodes parallel to, as opposed to perpendicular to, the target site, since the general structure of probe electrodes, specifically the exposed conductive portion, has not changed significantly since Bogduk et al's study. For example, Lord et al. (Neurosurgery 36(4):732-739, 1995) note that the electrodes must lie parallel to the nerve for the nerve to be incorporated in the radial lesion. In addition, Hooten et al. (Pain Medicine, 6(2):129-138, 2005) also conclude that, due to the characteristics of prior art probes and lesions formed therefrom, the probes should be placed parallel to the course of the target nerve in order to be effective.

A parallel approach may be difficult and time consuming for a user and it would therefore be advantageous to have a device capable of creating a lesion extending further distal to the probe, as well as a method describing a more perpendicular approach than has previously been possible. Thus, methods and devices that overcome some or all of the deficiencies associated with the prior art are desired.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

Figure 1A:
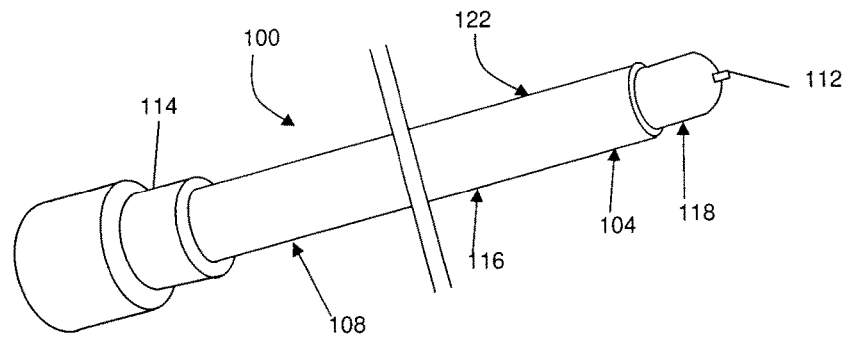
FIG. 1A is a perspective view of an embodiment of an apparatus of the present invention.

Embodiments of the invention described herein provide devices, systems, and methods which address some or all of the deficiencies of the current state of the art as described above. For example, in one broad aspect, embodiments of a device of the present invention may comprise an elongate member having one or more electrically insulated portions, and a distal face comprising one or more electrically exposed conductive portions for delivering energy substantially distal to the elongate member. At least one of the one or more electrically insulated portions may extend from a proximal region of the elongate member to the distal face.

In another broad aspect, a method is provided for creating a lesion at a target site within a body of a human or animal using an electrosurgical device. The method may comprise the steps of: inserting the electrosurgical device into the body such that the electrosurgical device is generally upstanding relative to the target site; and delivering energy from an energy source solely through a distal face of the electrosurgical device to the target site for creating the lesion at the target site.

In another broad aspect, embodiments of a device of the present invention may comprise a cannula having one or more electrically insulated portions and one or more electrically exposed conductive portions. The cannula may define one or more lumens. The device may further comprise an internally cooled elongate member sized to be disposed within one of the one or more lumens of the cannula, such that at least a portion of the elongate member is in electrical and thermal contact with the cannula.

In another broad aspect, embodiments of a device of the present invention may comprise a sterilizable electrosurgical device. In some embodiments, the device may comprise a sterilizable elongate member comprising one or more electrically insulated portions and one or more electrically exposed conductive portions. The elongate member may define at least one lumen. The device may further comprise at least one sterilizable connector at a proximal region of the elongate member. In another embodiment, the device may comprise a sterilizable elongate member having one or more electrically insulated portions and one or more electrically exposed conductive portions. The elongate member may define at least one lumen. The device may further comprise one or more sterilizable tubes associated with a proximal region of the elongate member, and at least one of the one or more sterilizable tubes may be operatively connected to the at least one lumen for delivering a fluid to the at least one lumen.

In another broad aspect, embodiments of the present invention may provide a method of delivering energy to a patient's body. The method may comprise the steps of: inserting at least one electrosurgical device into a patient's body, wherein the device has a longitudinal axis; positioning the at least one electrosurgical device such that the longitudinal axis of the device is generally upstanding relative to a target site within the patient's body; and delivering energy from the device to the target site, wherein the at least one electrosurgical device is cooled.

In another broad aspect, embodiments of the present invention may comprise a method of treating pain. The method may comprise, in any order, the steps of: introducing at least one electrosurgical device into a region of a patient's body; cooling the at least one electrosurgical device; and delivering energy through the at least one electrosurgical device to at least one target site within the region of a patient's body to affect at least one neural structure.

In another broad aspect, embodiments of the present invention may comprise a method for creating a lesion in order to affect at least one neural structure at a target site within a patient's body. The method may comprise, in any order, the steps of: determining one or more parameters of a lesion, such that the lesion created in accordance with the one or more parameters will affect the at least one neural structure; determining a length of an electrically exposed conductive portion of an electrosurgical device based on at least one of the one or more parameters of the lesion; inserting an electrosurgical device comprising an electrically exposed conductive portion having the determined length into the patient's body; and delivering energy to the target site through the electrosurgical device.

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1B:
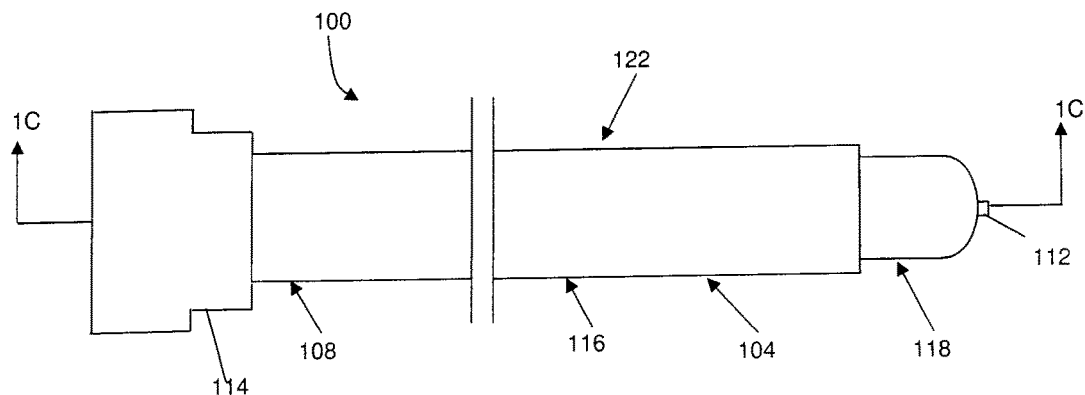
FIG. 1B is a top view of the embodiment of FIG. 1A.
Figure 1C:
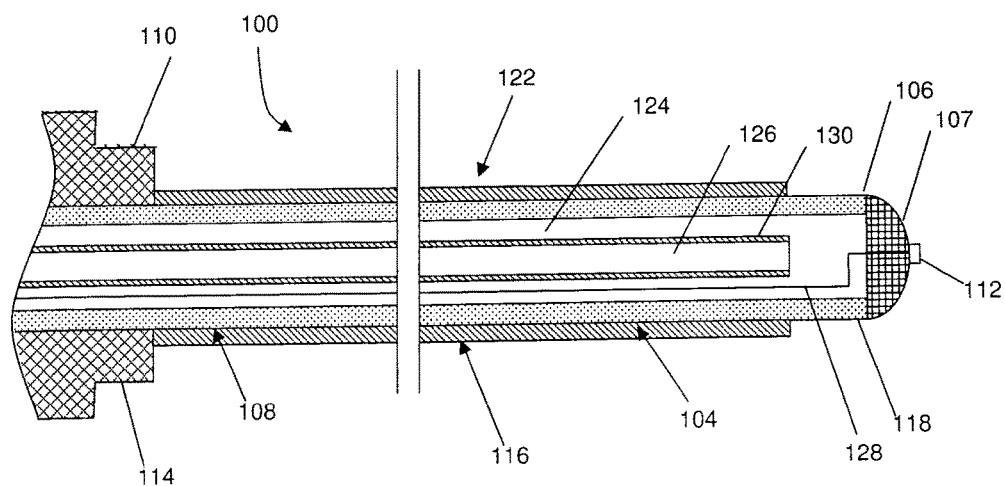
FIG. 1C is a cross-sectional view of the embodiment of FIG. 1A taken along the line 1C-1C in FIG. 1B.
Figure 2:
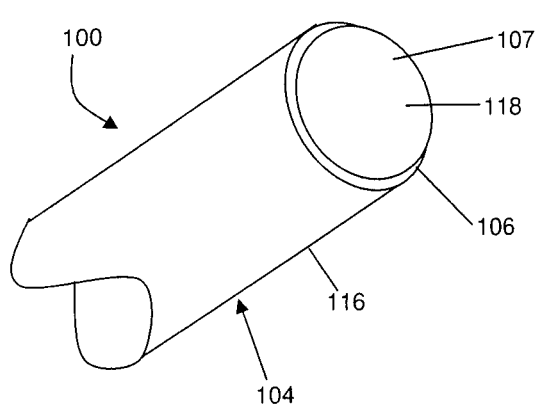
FIGS. 2A to 2D are perspective views showing configurations of electrically insulated portions and electrically exposed conductive portions of several embodiments of the present invention.
Figure 2:
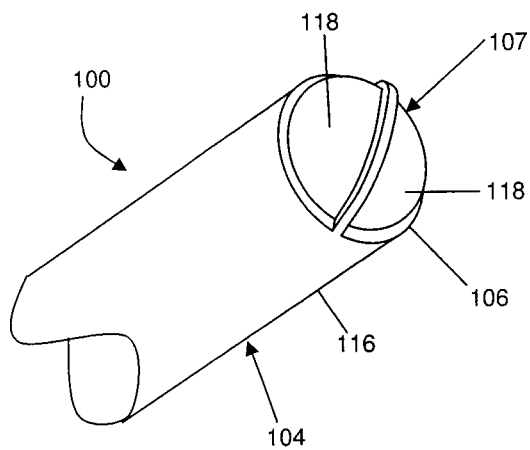
Figure 2:
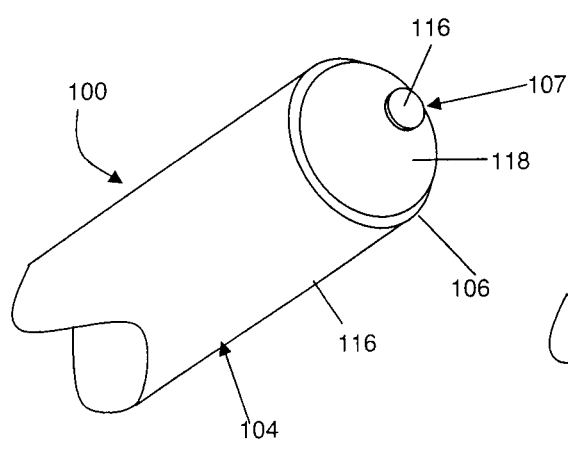
Figure 2:
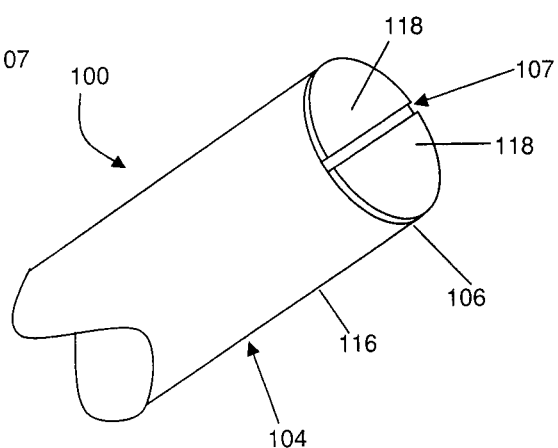

With reference first to FIG. 1A, a device of the present invention may generally comprise an electrosurgical instrument or device 100. As shown in the embodiment of FIGS. 1A to 1C, electrosurgical instrument or device 100 may be a probe 100; however, in other embodiments, electrosurgical instrument or device 100 may be a cannula, a catheter, or any other elongate member capable of delivering energy to a target site within a patient's body. For the sake of clarity, the term 'probe' is used throughout the specification to describe any such device. Probe 100 may be an elongate member, comprising a shaft 122, a distal region 104 a distal end 106, a distal face 107, a proximal region 108, and a proximal end 110. As used herein, the terms "distal" and "proximal" are defined with respect to the user and when the device is in use. That is, the term "distal" refers to the part or portion further away from the user, while the term "proximal" refers to the part or portion closer to the user, when the device is in use.

In some embodiments, probe 100 may define at least one lumen 124, as will be described hereinbelow. Furthermore, in some embodiments, either or both of distal end 106 and proximal end 110 may define at least one aperture, which may be in communication with lumen 124. In other embodiments, probe 100 may not define a lumen, and therefore may be described as substantially solid.

As shown in the embodiment of FIG. 1, probe 100 may comprise an electrically insulated portion 116 and an electrically exposed conductive portion 118. Electrically exposed conductive portion 118 may also be referred to as an active electrode, or when the exposed conductive portion is located at the distal end of probe 100, it may be referred to as an active tip. In general, electrically insulated portion 116 may extend from the proximal region of probe 100 to a location in the distal region of probe 100. The location to which electrically insulated portion 116 extends may depend on the application, as will be discussed hereinbelow. Furthermore, the location to which electrically insulated portion 116 extends may not be fixed, as will be discussed hereinbelow. In other embodiments, as shown in FIGS. 2A-2D, probe 100 may comprise more than one electrically insulated portion and/or more than one electrically exposed conductive portion.

Figure 6:
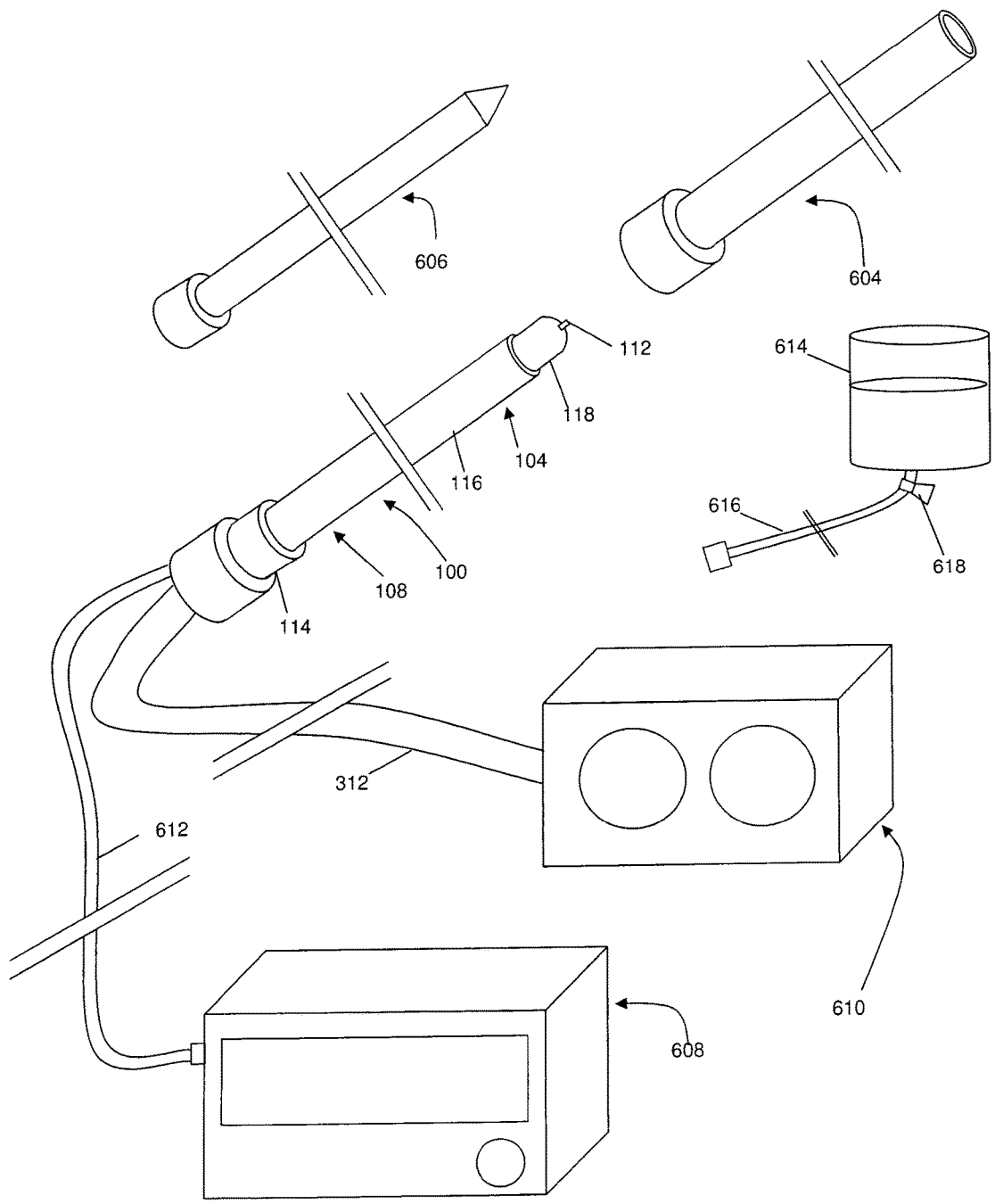
FIG. 6 is a perspective view of an embodiment of a system of the present invention.

In some embodiments, for example as shown in FIG. 1, the proximal region of probe 100 may comprise a hub 114. Hub 114 may be structured to operatively connect other devices such as connector cables, cannulae, tubes, or other hubs, for example, to probe 100. For example, as shown in FIG. 6 and discussed in further detail below, probe 100 may be coupled to an energy source and/or to a source of cooling via respective connecting means (for example, an electrical cable and/or flexible tubing) which may be associated with hub 114 (also shown in FIG. 3). Hub 114 may also serve as a handle or grip for probe 100. Hub 114 may be manufactured from a number of different materials, including, but not limited to, plastics, polymers, metals, or combinations thereof. Furthermore, hub 114 may be attached to probe 100 by a number of different means. For example, in one embodiment, hub 114 may be made from polypropylene, and may be attached to probe 100 by insert molding.

The size and shape of probe 100 may vary depending on the application, and the invention is not limited in this regard. For example, in some embodiments, the transverse cross sectional shape of probe 100 may be substantially circular. In other embodiments, the cross-sectional shape may be substantially polygonal, elliptical, or any other desired shape. In some embodiments, the length from distal end 106 to proximal end 110 of probe 100 may be between about 5 cm and about 40 cm and the outer diameter of shaft 122 may be between about 0.65 mm and about 2.00 mm (between about 20 AWG and about 12 AWG). In one specific example, the length of the probe may be about 7.5 cm, the outer diameter may be about 1.5 mm, and the transverse cross-sectional shape may be substantially circular. The shape of distal end 106 may vary depending on the application. Possible shapes include, but are not limited to, blunt, rounded, sharp, and beveled.

Probe 100 may be rigid or flexible and may be straight, bent or angled at one or more points along its length. As used herein, the term 'bent' refers to any region of non-linearity or any deviation from a longitudinal axis, gradual or abrupt, and at any angle. In embodiments wherein probe 100 is bent, the bend may be at various locations along probe 100, for example in distal region 104. Furthermore, the bend may be of a variety of degrees and lengths. For example, the bend may traverse about 25° of a circle, and occur over a length of about 5 mm. Furthermore, probe 100 may comprise a plurality of bends, which may or may not be in the same plane. For example, in some embodiments, probe 100 may be bent such that it is helical or 'corkscrew' shaped. In some embodiments, probe 100 may be structured such that its shape may be modified by a user before or during the course of a procedure. More specifically, the shape of distal region 104, for example, may be modified such that it may change from a straight to a bent configuration using an actuating mechanism. This may aid in accessing difficult to reach sites within the body. This may be accomplished by a variety of means, for example, probe 100 may comprise at least one active shape control mechanism, including but not limited to one or more pull-wires, a hydraulic or piezoelectric device, or another actuating mechanism.

In one embodiment, electrically insulated portion 116 may be formed by coating a portion of shaft 122 with an electrically insulative coating, covering, or sheathing. In other words, probe 100 may comprise electrically insulative material disposed on the surface of the elongate member. For example, in one embodiment shaft 122 of probe 100 may be fabricated from a biocompatible metal or alloy, for example stainless steel, which may be overlaid in part by an insulating coating, for example polytetrafluoroethylene (PTFE). In other embodiments, shaft 122 may be fabricated from another metal, such as nitinol or titanium, and/or another electrically insulating material, including but not limited to polyethylene terephthalate (PET), may be disposed thereon. In other embodiments, other metals or electrically insulating materials may be used, and the invention is not limited in this regard. Furthermore, the insulating material may be semi-porous, to allow for some leakage of current through the insulating material. In some embodiments, the material may also be a thermal insulator as well. In some embodiments, different insulating materials can be used for different portions of probe 100. The uncoated portion of the distal region of shaft 122 may serve as an conductive portion 118. The insulating coating may be applied to a portion of shaft 122 by dip-coating, spraying or heat shrinking, for example.

In another embodiment, the shaft 122 of probe 100 may be fabricated from an insulative or non-conductive material and may be furnished with one or more externally applied electrodes 118. In such embodiments, probe 100 may comprise one or more wires that may be attached to electrode(s) 118 at one end, and may run proximally along shaft 122, such that a proximal portion of the wire(s) may be operatively connected to an energy source, thereby supplying energy to electrodes 118. For example, shaft 122 may be fabricated from Radel® plastic, and the externally applied electrodes may be fabricated from stainless steel.

In alternate embodiments, shaft 122 may be manufactured from a combination of materials. For example, the distal region of shaft 122 may be made from a material such as nitinol, such that the shape of the distal region may be altered, and the remainder of shaft 122 may be made from stainless steel, such that the remainder of shaft 122 may be substantially fixed.

In some embodiments, probe 100 may be cooled. In some specific embodiments, probe 100 may be cooled by the internal circulation of a cooling fluid. Such a configuration, whereby a cooling medium does not exit from a distal region 104 of probe 100, may be referred to as an internally-cooled probe. The cooling fluid may be any fluid suitable for removing heat from probe 100 during surgery, for example water. Other examples of cooling fluid include, but are not limited to, liquid nitrogen and saline. Furthermore, the fluid may be at any temperature suitable for removing heat from the probe during surgery, for example between about 0° C. and about 25° C. More specifically, the temperature of the fluid may be at about room temperature (21° C.), about 4° C., or about 0° C., depending on the application.

In addition, the fluid may be delivered or circulated at a wide range of flow-rates, and the invention is not limited in this regard. An appropriate flow-rate may be determined or calculated based on a number of factors, including the conductivity and heat capacity of elongate member 100, the cooling fluid and/or the tissue, the internal structure of the probe, as described hereinbelow, and the desired temperature of distal end 106 of elongate member 100, among other factors. In some embodiments, the fluid may be delivered at between about 10 ml/min and about 30 ml/min.

Several embodiments of the internal structure of a probe cooled by the internal circulation of a cooling fluid are shown in FIG. 3. As shown in FIG. 3A, the shaft of probe 100 may define a first lumen 124, and the proximal end of probe 100 may be open and in communication with lumen 124. The distal end of probe 100 may be closed. Probe 100 may further comprise an internal tube, cylinder, or cannula 130 disposed within lumen 124, defining a second lumen 126. Internal tube 130 may have an open distal end, which may be located proximally to distal end 106 of probe 100, and an open proximal end. The proximal end of internal tube 130 may be structured to be operatively connected to a source of cooling fluid. For example, probe 100 may comprise a hub 308, which may connect internal tube 130 to a flexible tube 310. In an alternate embodiment, hub 114 may be structured to connect internal tube 130 to flexible tube 310, such that hub 308 is not required. Embodiments comprising hub 308, however, may be beneficial in that it may allow for tubing 310 to be removable. The proximal end of tube 310 may be connected to the cooling source, for example a reservoir of fluid, whereby tube 310 functions as an inflow tube for cooling fluid from the reservoir to probe 100. That is, tube 310 may function to deliver fluid to the distal region of probe 100. Thus, in use, fluid may flow from the reservoir of fluid, through the inflow tube 310, and into internal tubing 130. The fluid may subsequently exit the distal end of internal tubing 130, flow into lumen 124 of probe 100, and exit probe 100 via open proximal end 110. Open proximal end 110 may be coupled to means for returning the fluid to the reservoir. For example, another flexible tube 312 may operatively connect proximal end 110 to the reservoir, such that tube 312 functions as an outflow tube for the cooling fluid. In the embodiment shown in FIG. 3A, the first and second lumens 124 and 126 are coaxial; however, in other embodiments, second lumen 126 may not be centered about the longitudinal axis of probe 100, as shown in FIG. 3B. In an alternate embodiment, as shown in FIG. 3D, internal tube 130 may comprise one or more apertures 316, from which fluid may exit internal tube 130 and enter lumen 124 of probe 100. In this embodiment, internal tube 130 may extend to the distal end 106 of probe 100. In another embodiment, fluid may enter probe 100 via open proximal end 110, and exit probe 100 via tubing 130. That is, tube 310 may function to remove fluid from the distal region of probe 100.

Figure 3A:
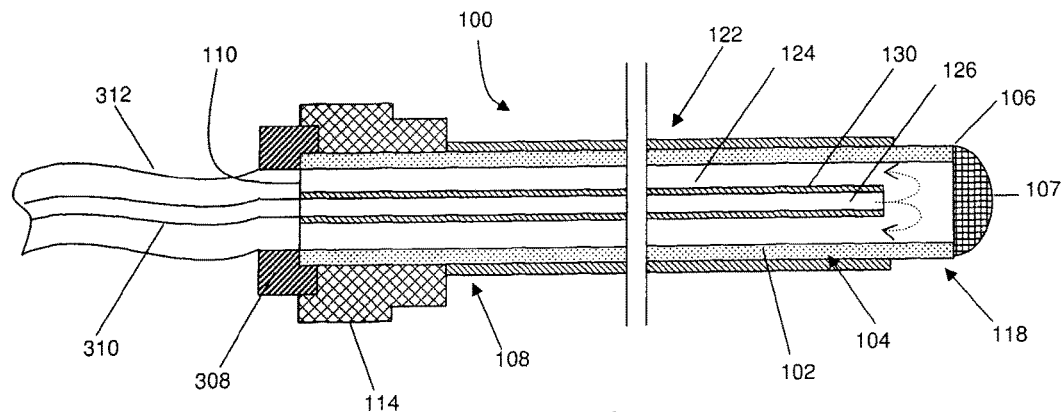
FIGS. 3A to 3E are cross sectional views of several embodiments of the present invention.
Figure 3B:
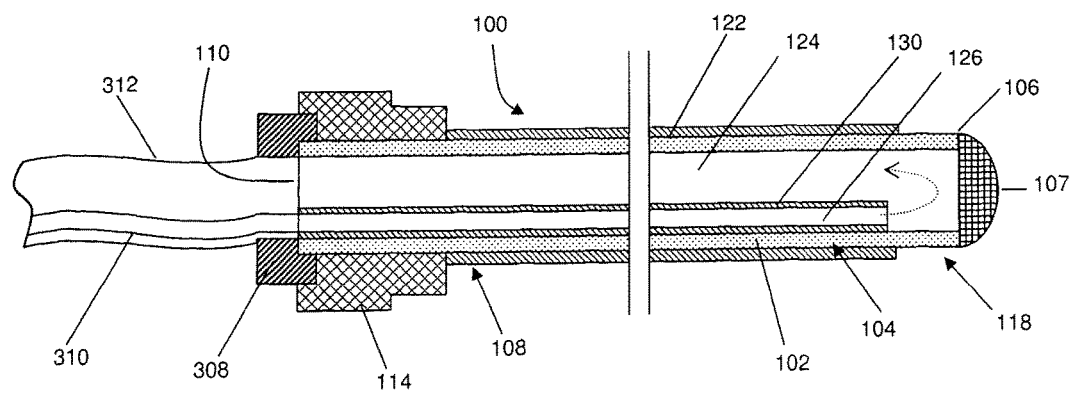
Figure 3C:
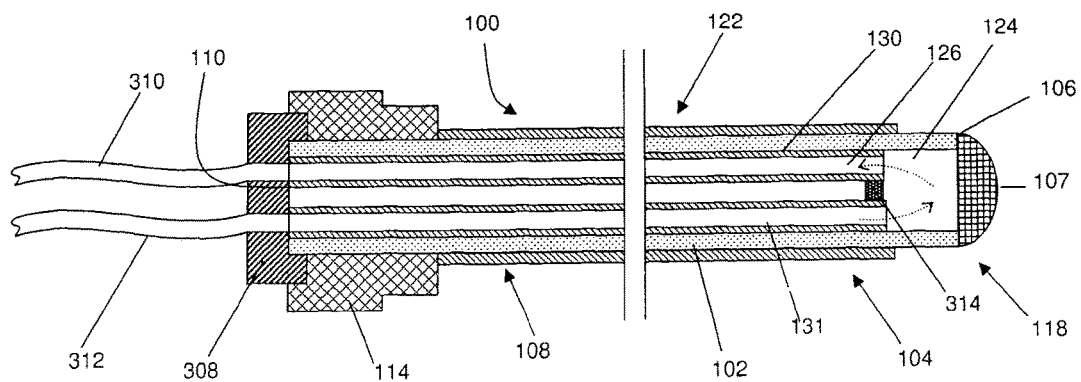
Figure 3D:
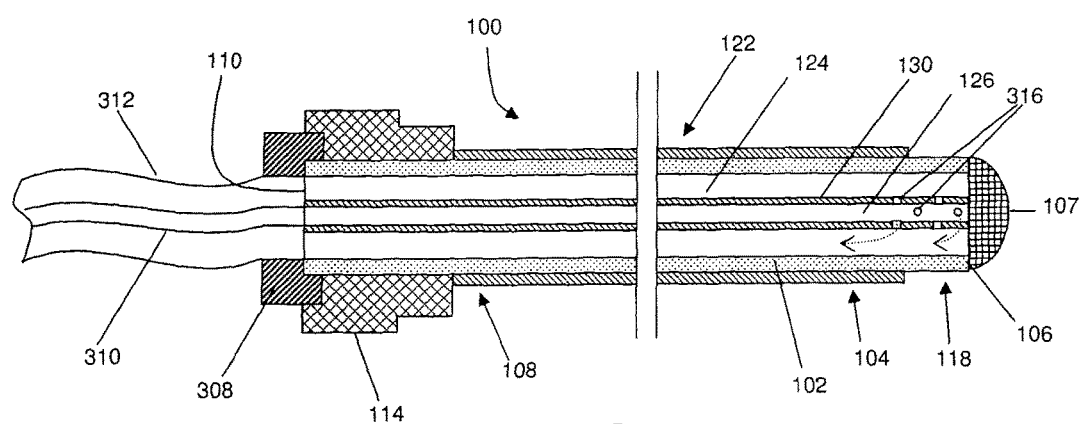
Figure 3E:
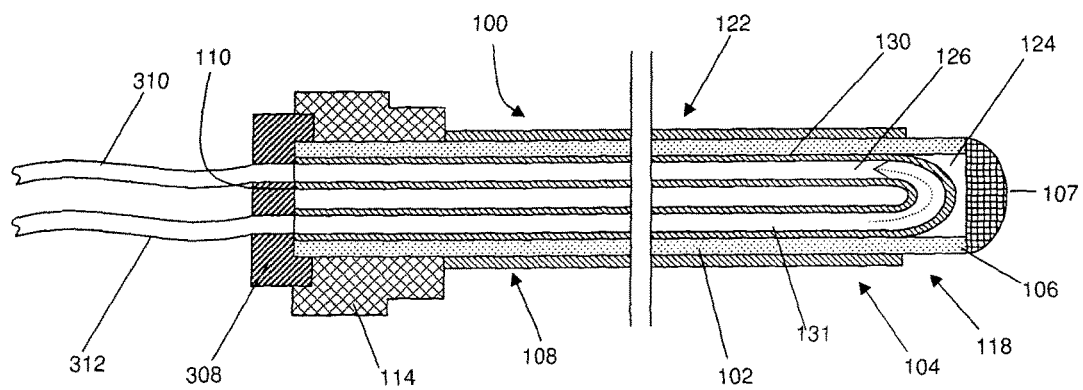

In another embodiment, as shown in FIG. 3C, probe 100 may comprise a plurality of inner tubes for the circulation of cooling fluid. For example, probe 100 may comprise first and second internal tubes 130, 131. Each internal tube 130, 131, may have an open distal end, which may lie proximally to the distal end of probe 100, and an open proximal end. The first internal tube 130 may deliver a cooling fluid from a reservoir to the distal region of probe 100. The cooling fluid may then return to the reservoir via the second tube 131. As described hereinabove, flexible inflow and outflow tubes 310, 312, may be provided which may operatively connect internal tubes 130, 131, to a reservoir of fluid or other source of cooling fluid. In an alternate embodiment, as shown in FIG. 3E, probe 100 may comprise a single inner tube 131, which may be substantially 'U' shaped, such that the cooling fluid enters and exits probe 100 from opposite ends of tube 131. In other embodiments, various quantities, orientations and/or configurations of internal tubes may be provided within probe 100.

In embodiments wherein probe 100 is bent, as described hereinabove, internal tubes 130 and/or 131 may be structured to accommodate the bend. For example, in one embodiment, internal tubes 130 and/or 131 may be bent at a similar location and angle as probe 100. In another embodiment, internal tubes 130 and/or 131 may end at a location that is proximal to the location where probe 100 bends. In embodiments wherein the shape of probe 100 is structured to be modified before or during a procedure, internal tubes 130 and/or 131 may be structured such that their shape is also modified along with probe 100.

In alternate embodiments, fluid exiting probe 100 may not be returned to the source of cooling, but may rather be removed to another location, for collection and/or disposal of the fluid.

In some embodiments, a flow impeding structure 314 may be used to restrict the flow of cooling fluid within probe 100. For example, in the embodiment shown in FIG. 3C, a plug 314 may optionally be used to fill a portion of lumen 124, such that any cooling fluid supplied to probe 100 that is not located within one of the internal tubes 130, 131, is confined to a distal region of probe 100. In other words, cooling fluid may flow from a reservoir, through first internal tube 130, to distal region 104 of probe 100. The cooling fluid may then circulate within the portion of lumen 124 that is distal to the plug 314 in order to provide cooling to the distal region of probe 100. The cooling fluid may then exit probe 100 through second internal tube 131 and return to the reservoir. In some embodiments, plug 314 may be made of a radiopaque material, for example silver solder, such that plug 314 may also function as a radiopaque marker when visualized using fluoroscopic imaging. In alternate embodiments, other materials may be used for plug 314 instead of silver solder, and the invention is not limited in this regard.

Means for cooling probe 100 may include, but are not limited to, circulation of a cooling fluid, for example as described above, cooling by a thermoelectric circuit, or chemical cooling by an endothermic reaction. In some embodiments, probe 100 may be cooled by a thermoelectric circuit. For example, probe 100 may partially or fully house a circuit comprising two dissimilar metals or semiconductors, for example P- and N-doped bismuth-telluride, which are joined together at two junctions. When current passes through the circuit, heat may be transferred from one junction to the other. This phenomenon is known as the Peltier Effect. The junction where the heat is transferred from may be located in the distal region of probe 100, and the junction where the heat is transferred to may be located at a proximal region of probe 100 or externally to probe 100. Energy may be provided to the circuit by an external energy source (for example, the same energy source that delivers RF energy to probe 100), an electrical generator or a battery, for example.

In an alternate embodiment, probe 100 may be cooled chemically. For example, probe 100 may comprise two internal tubes, similar to the structure shown in FIG. 3C. The proximal end of the tubes may each be operatively connected to a separate reservoir of material. The distal end of each tube may deliver material from each respective reservoir to the distal region of probe 100. The materials in the separate reservoirs may be selected such that when mixed, an endothermic reaction or endothermic mixing occurs. Thus, when each material exits its respective internal tube and reaches the distal region of probe 100, the materials will mix, thermal energy will be absorbed, and the distal region of the probe will be cooled. The product(s) of the endothermic reaction or the resulting mixture may exit probe 100 via open proximal end 110. One example of a suitable reaction for the chemical cooling of probe 100 may be the mixing of water and tetrahydrofuran, however because of the toxicity of chemicals of this nature, suitable precautions may have to be taken to ensure no leakage during use.

As mentioned hereinabove, one or more fluids may be delivered from a reservoir to lumen 124 of probe 100 for the purposes of cooling probe 100. The fluid(s) may be delivered to the probe via a number of means, and the invention is not limited in this regard. For example, in one embodiment, the reservoir of fluid may comprise a container, for example an intravenous (IV) bag 614, which is elevated above the patient. Tubing 616, for example clear plastic flexible tubing, may be used to connect the reservoir to an inlet in probe 100. A valve 618 may be placed at the junction of the container and the tubing (or at some other location between the container and the probe), such that when the valve is opened, gravity may cause fluid to flow towards probe 100. After circulation within probe 100, fluid may exit probe 100 via tubing similar to tubing 312, which may drain into another reservoir, for example a second IV bag. In another embodiment, at least one pump may be used to deliver fluid to the probe. For example, at least one peristaltic pump 610, shown in FIG. 6, may be operatively connected to a reservoir of fluid. The reservoir of fluid may be an IV bag, a polypropylene vial or burette, or another container, for example. The pump(s) may pump the fluid from the reservoir to an inlet in probe 100. After circulating in probe 100, the fluid may exit the probe through an outlet in probe 100 and may flow through a tube to either the same or a different reservoir or, alternatively, to an alternate location as described above. A second pump, gravity, or a source of suction, for example, may assist in drawing the fluid out of the probe.

Tubing 310 and 312 may be made from a variety of materials. For example, tubing 310, 312, may be fabricated from a flexible plastic material, such as Tygon (trademark), polyvinylchloride (PVC) or polycarbonate. In some embodiments, tubing 310 and 312 may comprise markings or other means of identification, such that the inflow tubing is distinguishable from the outflow tubing. Further details regarding this concept are disclosed in U.S. patent application Ser. No. 11/105,527 (filed on Apr. 14, 2005), previously incorporated herein by reference.

In some embodiments, elongate member 100 may be sterilizable. In these embodiments tubing 310 and 312 may or may not be sterilizable as well. The elongate member may be capable of being sterilized by, for example, steam, ethylene oxide, or radiation sterilization without risk of material degradation or discoloration. In order for elongate member 100 to be sterilizable, elongate member 100 may be made from sterilizable materials, for example, shaft 122 may be made from stainless steel and the electrically insulative coating may be made from PTFE. In embodiments wherein tubing 310 and 312 are sterilizable, tubing 310 and 312 may be made from medical/surgical Tygon tubing. In other embodiments, tubing 310 and 312 may be detachable from probe 100, and therefore may not be required to be sterilizable. In this embodiment, probe 100 may comprise at least one connector, which may be sterilizable, for connecting probe 100 to tubing 310 and 312, or another fluid source. The at least one connector may comprise means for securing a fluid source to the elongate member, for example a luer lock, which may fit between tubing 310 and 312 and lumen 124, thus allowing for fluid communication between tubing 310 and 312 and lumen 124. In one embodiment, elongate member 100 may comprise two sterilizable connectors, one of which may couple a tube for inflowing fluid to one of lumen 124 and internal tube 130, and the other of which may couple a tube for outflowing fluid to the other of lumen 124 and internal tube 130.

Figure 4A:
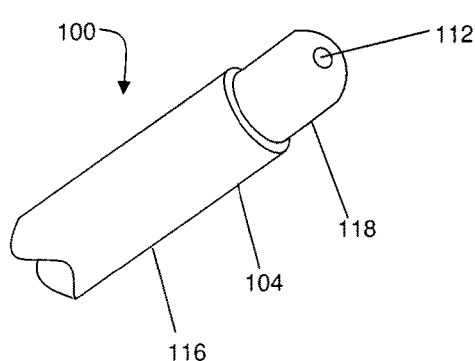
FIGS. 4A to 4C are partial perspective views showing configurations of temperature measuring devices for several embodiments of the present invention.
Figure 4B:
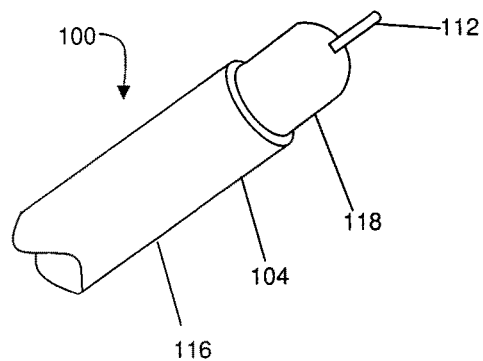
Figure 4C:
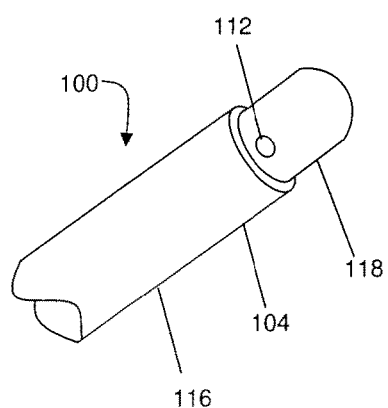

In some embodiments, probe 100 may comprise at least one temperature sensing device 112, i.e. a temperature sensor. Temperature sensing device 112 may be any means for sensing and/or measuring temperature, including, but not limited to, a thermocouple, a thermistor, an optical fluorescence sensor, and a resistance thermometer. In some embodiments, temperature sensing device 112 may be positioned at the distal region of probe 100, for example at distal end 106. As shown in the embodiments of FIGS. 4A to 4C, temperature sensing device 112 may have various configurations. For example, as shown in FIG. 4A, temperature sensing device 112 may be disposed at the distal end 106, and may be substantially flush with the distal end. In another embodiment, as shown in FIG. 4B, temperature sensing device 112 may protrude from distal end 106, such that it may measure the temperature of a material that is located distally to distal end 106, rather than the temperature of probe 100 itself or of material adjacent to probe 100. In another embodiment, as shown in FIG. 4C temperature sensing device 112 may be located proximally to distal end 106. In further embodiments, probe 100 may comprise additional temperature sensing devices. For example, a first temperature sensing device may be located at the distal end of probe 100, and a second temperature sensing device may be located distally from the distal end of probe 100, such that the temperature at the distal and of the probe as well as in the tissue may be measured. In other embodiments, other configurations are possible, and the invention is not limited in this regard. Furthermore, in the embodiments shown in FIGS. 4A and 4C, the temperature sensing device may be located within the probe, or on the external surface of the probe.

In an alternate embodiment, temperature sensing device 112 may be located within lumen 124 of probe 100 so as to measure the temperature of a cooling fluid. By monitoring the change in temperature of the cooling fluid, which relates to the amount of heat being drawn away from the probe, the temperature of the tissue located adjacent conductive portion 118 may be determined.

In another embodiment, probe 100 may comprise an extendible remote temperature sensing element which may be deployed from probe 100. An extendible temperature sensing device 112 may allow monitoring of the temperature within tissues located remotely from the surface of conductive portion 118. The extendible temperature sensing device 112 may further be steerable so that its position may be changed during a procedure to obtain temperature measurements from a variety of tissue regions.

In some embodiments, probe 100 may comprise means for operatively connecting temperature sensing device 112 to an external device. In some embodiments, such a device may be a display or screen, such that the temperature measured by the temperature sensing device may be viewed by a user. In other embodiments, the external device may be an electrical generator, such that temperature feedback may be provided to the electrical generator. Means for operatively connecting temperature sensing device 112 to an external device may comprise an insulated wire 128, which may extend proximally from temperature sensing device 112, through a lumen of probe 100, and out of probe 100 through proximal end 110. Wire 128 may be any temperature or electrical conductor capable of operatively connecting temperature sensing device 112 to an external device. Alternatively, temperature sensing device 112 may be operatively connected to an external device via a wireless connecting means, including, for example, infrared or Bluetooth (trademark). Further details regarding temperature sensing devices may be found in U.S. Patent Application Publication 2005/0177209 (published on Aug. 11, 2005), incorporated herein by reference.

In some embodiments, electrosurgical instrument or device 100 may comprise a sensor for measuring impedance. As the impedance of a tissue may be a characterizing factor, measuring the impedance of tissue proximal to the probe can help confirm placement within a desired tissue type. In some embodiments, probe 100 may be structured to measure the electrical impedance between, for example, two points on probe 100 or between a point on conductive portion 118 and a point on an auxiliary device such as a cannula or a grounding pad. Further details regarding impedance measuring means may be found in U.S. Patent Application Publication 2005/0177209 (published on Aug. 11, 2005), incorporated herein by reference.

In some embodiments, probe 100 may comprise a sensor for measuring pressure. The means of measuring pressure may comprise a lumen in fluid communication with fluid in a patient's body as well as with a pressure transducer to record the pressure measurements. In other embodiments, the pressure sensor may comprise a pressure transducer disposed at a desired location on probe 100.

As mentioned above with respect to the temperature sensing device, probe 100 may comprise means for operatively connecting any impedance or pressure measuring means to an external device. For example, a pressure transducer may be electrically coupled to a wire located within probe 100, which wire may be further electrically coupled to an external device to transmit a signal from the pressure transducer to the external device.

In some embodiments, probe 100 may comprise means for enhancing the visualization thereof, for example when viewed under fluoroscopic imaging or another imaging modality. Such means may be a visible marker, a radiopaque marker or markers for use with magnetic resonance imaging or ultrasound, for example. Further details regarding enhanced visualization are disclosed in U.S. patent application Ser. No. 10/382,836 (filed on Mar. 7, 2003), and Ser. No. 11/079,318 (filed on Mar. 15, 2005), both of which are incorporated herein by reference.

In some embodiments, hub 114 may have markings to indicate, for example, the direction/orientation of a bend or curve of probe 100 or the location of an aperture or a temperature or pressure sensing device on or within probe 100. These markings may be visual indicators, or tactile indicators, which may be textured or raised so that the user may see or feel the markings while manipulating probe 100.

As has already been mentioned above, in some embodiments probe 100 may be furnished with at least one aperture, which may be in fluid communication with lumen 124. Such an aperture may be a lateral port defined by a side wall of probe 100 providing an outlet for the delivery of cooling fluid, anesthetic, or any other treatment compound to a target treatment site in a body. Alternatively, the at least one aperture may be located at the distal end of probe 100.

In some embodiments, a proximal end of probe 100 may comprise a strain relief, which may additionally comprise a grip running from the proximal end to the distal end of the strain relief. A strain relief may be, for example, a soft flexible bend relief able to support any cable or tubing exiting the proximal end of probe 100.

As mentioned hereinabove, the size and/or geometry of electrically insulating region 116 and conductive portion 118 may differ depending on the specific application. As disclosed in U.S. Provisional Patent Application 60/743,511 (Filed on Mar. 16, 2006), and 60/595,559 (Filed on Jul. 14, 2005), previously incorporated herein by reference, when sufficient energy is delivered from an energy source through an active electrode to a tissue of a patient's body, a lesion may form in the tissue wherein the size, shape, and location of the lesion are at least partially dependent on the size and/or geometry of the active electrode.

Figure 5A:
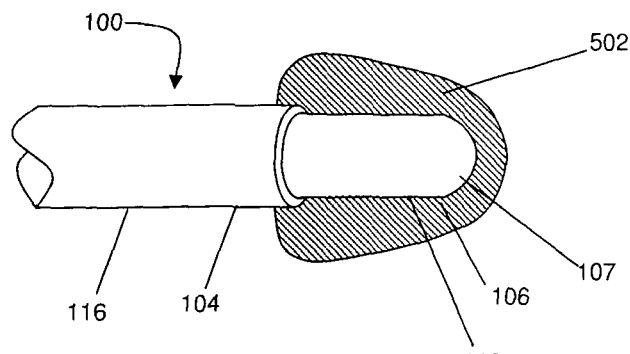
FIGS. 5A to 5D are partial perspective views showing embodiments of a distal region of a probe of the present invention and examples of lesions formed therefrom.

Exemplary embodiments of probes 100 having a conductive portion 118 of various geometries, and being of between about 16 AWG and about 19 AWG, and examples of lesions 502 that may be formed therefrom are illustrated in FIGS. 5A to 5D, by way of non-limiting example only. Referring first to FIG. 5A, when conductive portion 118 of probe 100 is elongate, for example having a length of between about 4 mm and about 6 mm a substantially oblate lesion 502 may form around conductive portion 118. Due to edge effects, the distribution of energy may not be equal around all portions of conductive portion 118, and a large portion of the current may exit conductive portion 118 in the region closest to electrically insulated portion 116. Thus the widest portion of the lesion may form in the area adjacent electrically insulated portion 116. In use, such a conductive portion may be positioned such that it lies substantially parallel to the surface of the tissue to be lesioned (target site) in order to provide maximum efficacy.

Figure 5B:
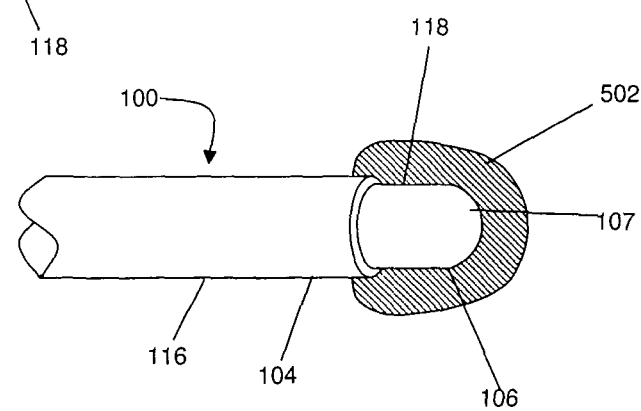

Referring now to FIG. 5B, when electrically conductive portion 118 of probe 100 is shortened, for example having a length of between about 2 mm and about 4 mm, a substantially more rounded lesion 502 may form around conductive portion 118. Due to the shorter length of conductive portion 118, lesion 502 may extend distally further from probe 100 than the lesion shown in FIG. 5A.

Figure 5C:
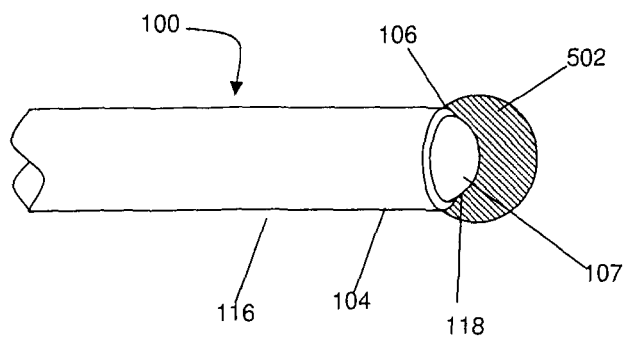
Figure 5D:
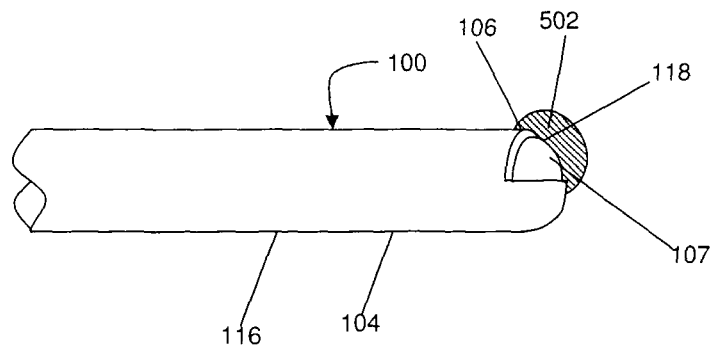
Figure 15:
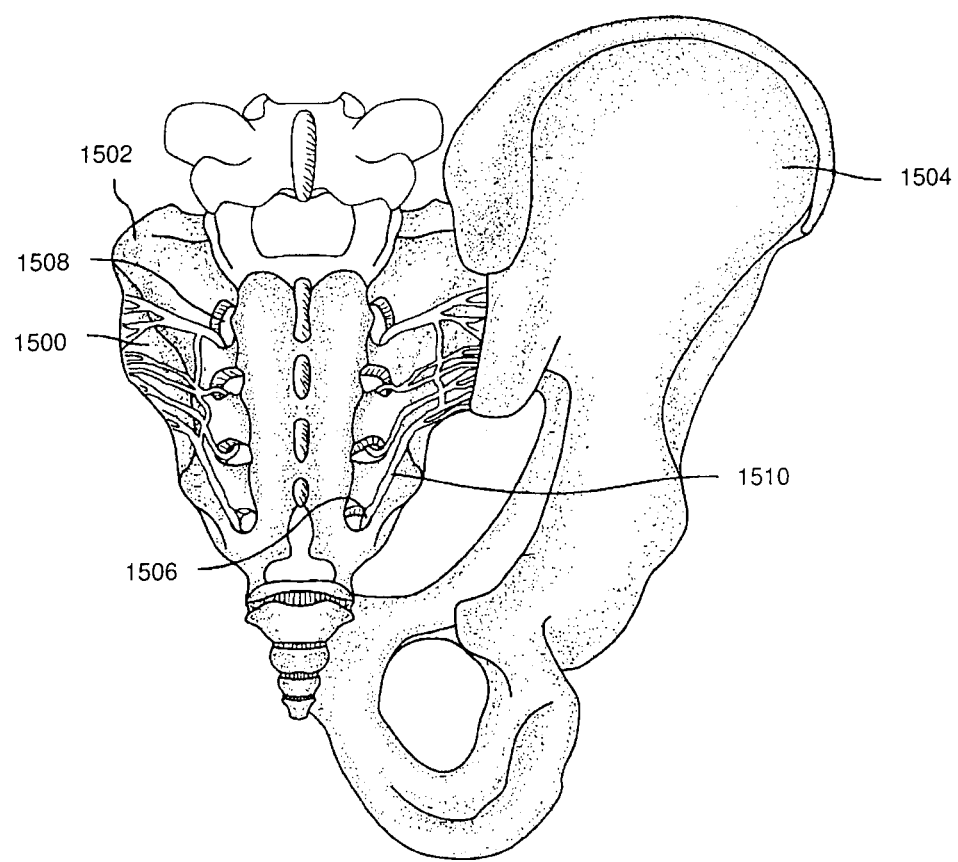
FIG. 15 shows a plan view of the sacroiliac region of a human.
Figure 16A:
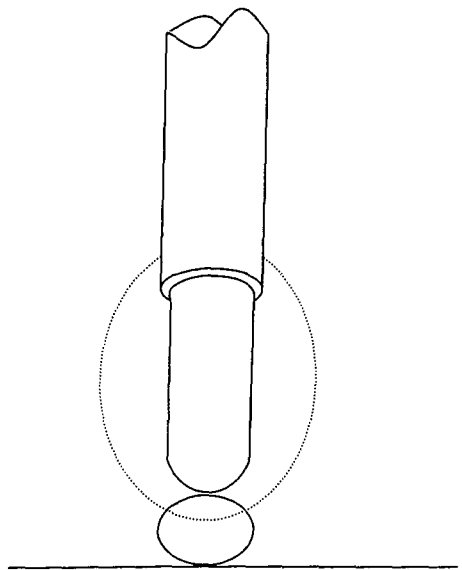
FIG. 16 shows a lesion as would be formed by a probe of the prior art.
Figure 16B:
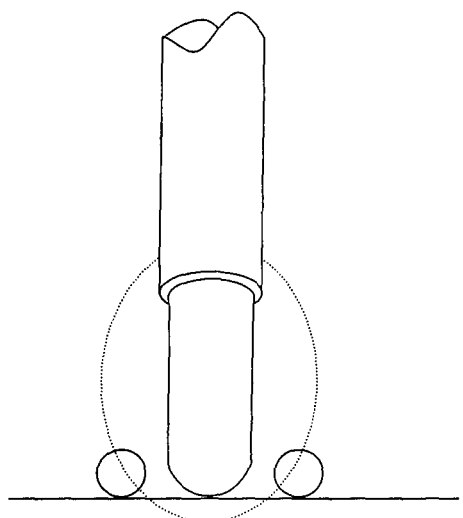
Figure 16C:
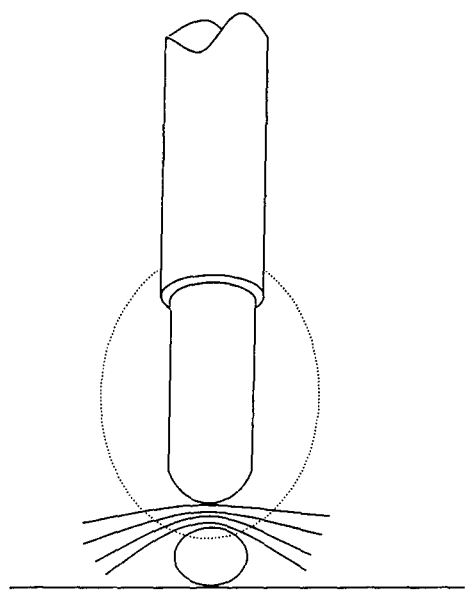

In some embodiments, the electrically insulated portion may extend substantially from the proximal region of probe 100 to the distal end of probe 100. For example, the electrically insulated portion may terminate at the distal face of the probe such that distal face 107 of probe 100 comprises at least one electrically exposed conductive portion. As will be apparent to the person skilled in the art, depending upon the geometry of the probe, the electrically insulated portion may terminate slightly proximal to the distal face so long as the energy delivery remains substantially distal. In some embodiments, a portion of distal face 107 may comprise at least one conductive portion 1118 as shown, for example, in FIGS. 2B-2D. Referring now to FIG. 5C, a probe 100 having a distal face 107 that comprises electrically exposed conductive portion 118 is shown. In such embodiments, if distal face 107 is rounded (as shown in FIG. 5C), the rounded face or surface may comprise the conductive portion; if the distal face 107 is flat, the flat surface may comprise the conductive portion, and so on. In these embodiments, a lesion 502 may form wherein the lesion forms substantially distal to the distal face 107, for example such that the majority of lesion 502 is located distal to the distal face 107 of the probe, and the shape of lesion 502 may be substantially rounded, for example the ratio of the length of the lesion (i.e. the dimension along the longitudinal axis of the probe) to the width of the lesion (i.e. the dimension perpendicular to the longitudinal axis of the probe) may be about 1:1. In use, such a probe 100 may be positioned such that it is oriented substantially perpendicular or generally upstanding to the target site or surface of the tissue to be lesioned, i.e. such that the tissue to be lesioned is generally distal to the probe 100, whereby the lesion may extend distally from the probe 100 to the target tissue. This can provide significant advantages in a region of the body such as the sacroiliac region (shown in FIG. 15) having a rough or uneven surface, because the conductive portion 118 can be positioned to lesion tissue disposed in rifts and valleys between bony structures, or in fissures or grooves in the surface of a bony structure, as is described in detail below. In further embodiments the conductive portion may be offset from an axis of the probe 100 such that the electrically exposed conductive portion 118 is not symmetrical about the axis of the probe 100, as shown for example in FIG. 5D.

In some embodiments, probe 100 may be structured to have a conductive portion of a fixed size. In other embodiments, the size of the conductive portion may be adjustable. For example, in one embodiment, wherein probe 100 comprises a conductive shaft with an electrically insulative sheath or coating disposed thereon, the electrically insulative sheath may be structured such that it may be slid or otherwise moved distally or proximally along the shaft. Thus, when the electrically insulative sheath is moved proximally along the shaft, the electrically exposed portion, or active electrode, would become longer. When the electrically insulative coating is moved distally on the shaft, the active electrode would become shorter. As mentioned above, altering the length of the active electrode may affect the geometry of a lesion formed therefrom. In some embodiments, the length of the active electrode may be modified before, during or after a treatment procedure while, in other embodiments, the length of the active electrode may not be modified during the actual course of the procedure. For example, in one such embodiment, the probe may have a safety mechanism, for example a stopping means such as a clamp, to prevent movement of an insulative sheath during the course of a treatment procedure.

In another alternate embodiment of the present invention, a treatment apparatus may comprise a cannula, in addition to a probe. The cannula may be used to deliver energy to the patient's body, as will presently be described, and/or the cannula may be used to facilitate insertion of the probe, as will be described hereinbelow. In embodiments wherein the cannula is used to deliver energy, the cannula may comprise at least one electrically exposed conductive portion and at least one electrically insulated portion. In some embodiments, the body of the cannula may be constructed from a conductive material, which is at least partially overlain with an insulating sheath or coating, defining the insulating region; however, in some embodiments, the cannula may be constructed from an insulating material with one or more conductive bodies or electrodes applied externally. The distal end of the cannula may be pointed or sharp. For example, the distal end of the cannula may comprise a bevel. In one embodiment, the at least one electrically insulated portion may extend from the proximal region of the cannula to the distal end of the cannula, such that the distal face of the cannula comprises at least one exposed conductive portion. In embodiments comprising a bevel, the at least one exposed conductive portion may comprise the bevel. In alternate embodiments, the exposed conductive portion may, alternatively or in addition, be located on a side of the cannula. In some embodiments, the electrical insulation may extend to the heel of the bevel of the cannula while in others the insulation may end further proximally along the cannula.

In some embodiments, the cannula is straight, whereas in some other embodiments the cannula may be bent. For example, in some such embodiments, the cannula may have about a 5 to about a 20 degree bend in the distal region of the cannula. In some embodiments, the cannula may be between about 16 and about 18 AWG, between about 75 and about 150 mm in length, with the electrically exposed conductive portion about 2 mm to 6 mm in length. In these embodiments, the probe may be structured to be disposed within the lumen of the cannula, and to be in electrical contact with the cannula when fully disposed within the cannula.

The probe may comprise an electrically conductive elongated shaft, a connecting means for connecting to an energy source, and a connecting means for connecting to a cooling supply, for example as described herein above. Thus, when energy is supplied by an energy source to the probe, the energy flows along a conductive portion of the cannula and is delivered to the target treatment site, traveling through the tissue or body to a reference or return electrode. In such embodiments, the shaft of the probe may be electrically conductive and exposed along substantially the entire length of the probe. In other words, a probe used in such an embodiment in conjunction with a cannula may not comprise an electrically insulative coating as described above.

In some embodiments, the distal end of the probe may be substantially flush with the distal end of the cannula when fully disposed in the cannula. In other embodiments, the distal end of the probe may extend distally from the distal end of the cannula when fully disposed in the cannula. In other embodiments, the distal end of the elongate member may be recessed proximally from the distal end of the cannula when fully disposed in the cannula. As used herein, the phrase 'fully disposed' refers to a first member being substantially fully received within a second member such that, under normal use, it is not intended to be inserted into the second member any further.

The probe and cannula may be structured such that when the probe is fully disposed within the cannula, at least a portion of the probe is electrical and/or thermal contact with at least a portion of the cannula, such that thermal and/or electrical energy may be delivered from the probe to the cannula. This may be accomplished by flushing the cannula with a fluid such as saline prior to inserting the probe, such that a layer of fluid remains between at least a portion of the probe and cannula. The saline may then serve to conduct electricity and/or heat between the probe and the cannula. Alternatively, the probe and cannula may be structured such that they are in physical contact when the probe is fully disposed within the cannula, thereby also being in electrical and thermal contact. In a further embodiment, a portion of the probe may be in thermal contact with the conductive portion of the cannula. This may be beneficial in that the cooling of the probe would allow for the conductive portion of the cannula to be cooled. The probe may be cooled by a variety of methods, as described hereinabove.

In certain embodiments, it may be desired to utilize a probe of this embodiment with preexisting cannulae. Thus, it may be desirable to provide a probe within a certain range of outer diameters, for example between about 24 AWG and about 31 AWG. A probe of this embodiment may therefore comprise a single internal lumen, for example as shown in FIGS. 3A and 3D, such that the outer diameter of the probe may remain substantially small. In other embodiments, the probe may comprise two or more internal lumens, which are each of a certain size such that the probe may remain between about 24 and about 31 AWG. At least one conductive portion on the exterior of the probe may come in contact with at least one conductive portion on the interior of the cannula continuous with or electrically coupled to at least one conductive portion on the exterior of the cannula. Further details regarding such embodiments are disclosed in U.S. Provisional Patent Application 60/595,560 (filed on Jul. 14, 2005), incorporated herein by reference.

Embodiments comprising a cooled probe within a cannula may be advantageous in that pre-existing cannulae may be used in conjunction with such embodiments of a cooled probe. Examples of such cannulae include the Baylis Pain Management Radiofrequency Cannula of Baylis Medical Company Inc. (Montreal, Canada). Thus, these probe embodiments may allow for use of a cannula that is similar to those currently in use and familiar to practitioners, but which can be used to create larger lesions than presently possible due to the cooling supplied to the probe disposed within the cannula. In addition, practitioners may be familiar with a procedure involving positioning the distal region of a cannula at a target site, positioning a probe within the cannula, and delivering energy from the probe to the cannula, and from the cannula to the target site. Thus, a cooled probe of this embodiment, sized to be disposed within a cannula, would allow practitioners to follow a normal procedure with the added benefit of cooling, similar to what they have previously practiced using a similar cannula though without cooling.

With reference now to FIG. 6, systems of the present invention may comprise one or more of: one or more probes 100; one or more introducer apparatuses; one or more dispersive return electrodes (not shown); one or more sources of cooling, for example pumps 610; one or more energy sources, for example generators 608; and one or more connecting means, for example tubes 312 and/or cables 612.

The introducer apparatus may aid in inserting probe 100 into a patient's body. The introducer apparatus may comprise a hollow elongate introducer or cannula 604 and an obturator 606. In this embodiment, as mentioned hereinabove, cannula 604 may be useful for facilitating insertion of the device into the patient's body. For example, cannula 604 and/or obturator 606 may be substantially stiff or rigid, such that the introducer apparatus may assist in piercing skin or other body tissues. Obturator 606 may be structured to cooperatively engage with cannula 604. In other words, obturator 606 may be sized to fit within the lumen of cannula 604 and may comprise means for securing obturator 606 to cannula 604. In one embodiment, when obturator 606 is fully disposed within cannula 604, obturator 606 sufficiently occludes the lumen of cannula 604 such that tissue is prevented from entering the lumen when the introducer apparatus is inserted into the body. In some embodiments the distal end of obturator 606 may be sharp or pointed. In these embodiments, the distal end of obturator 606 may be conical, beveled, or, more specifically, tri-beveled. The lengths of obturator 606 and cannula 604 may vary depending on the application. In one embodiment, cannula 604 may be sized such that its distal end can reach the target tissue within the body while the proximal end remains outside of the body. In some embodiments, cannula 604 may be between about 5.5 inches (13.97 cm) and about 7.5 inches (19.05 cm) in length, and obturator 606 may be between about 5.5 inches (13.97 cm) and about 7.5 inches (19.05 cm) in length. More specifically, cannula 604 may be about 6.4 inches (16.26 cm) in length, and obturator 606 may be about 6.6 inches (16.76 cm) in length. Obturator 606 may be slightly longer than cannula 604, so that the distal end of obturator 606 may protrude from cannula 604 when fully disposed. In some embodiments, obturator 606 may be substantially longer than cannula 604, and may be visible under fluoroscopy, such that it may aid in visualizing the location of lesion formation when a cooled probe is used. Further details regarding this embodiment are disclosed in U.S. Provisional Patent Application 60/744,518 (filed on Apr. 10, 2006), incorporated herein by reference. The lumen of cannula 604 may also be sized to accommodate the diameter of probe 100, while remaining as small as possible in order to limit the invasiveness of the procedure. In a specific embodiment, the proximal regions of cannula 604 and obturator 606 are structured to be locked together with a hub or lock.

In one embodiment, cannula 604 and obturator 606 may be made from stainless steel. In other embodiments, cannula 604, obturator 606, or both may be made from other materials, such as nickel-titanium alloys for example. Furthermore, in some embodiments, obturator 606 may comprise a means for connecting obturator 606 to generator 608, for example a wire or cable. In such embodiments, obturator 606 may be operable to measure the impedance of tissue as the introducer apparatus is inserted into the patient's body. In addition or alternatively, obturator 606 may be operable to deliver stimulation energy to a target tissue site, as described further herein below.

In some embodiments, probe 100 may be structured to be operatively connected to an energy source 608, for example a generator 608. Connecting means 612 for connecting probe 100 to generator 608 may comprise any component, device, or apparatus operable to make one or more electrical connections, for example an insulated wire or cable. In one embodiment, connecting means 612 may comprise an electrical cable terminating at hub 114 as well as a connector at a proximal end thereof. The connector may be operable to couple to energy source 608 directly or indirectly, for example via an intermediate cable. At least one wire or other electrical conductor associated with cable 612 may be coupled to a conductive portion of shaft 122, for example by a crimp or solder connection, in order to supply energy from energy source 608 to shaft 122. In one specific embodiment, a 4-pin medical connector may be used to connect cable 612 to an intermediate cable (not shown), which may be further attached to a 14-pin connector capable of being automatically identified when connected to generator 608.

Generator 608 may produce various types of energy, for example microwave, ultrasonic, optical, or radio-frequency electrical energy. In some embodiments, generator 608 may produce radiofrequency electrical current, having a frequency of between about 10 kHz and about 1000 kHz, at a power of between about 1 W and about 50 W. In some embodiments, generator 608 may comprise a display means incorporated therein. The display means may be operable to display various aspects of a treatment procedure, including but not limited to any parameters that are relevant to a treatment procedure, such as temperature, power or impedance, and errors or warnings related to a treatment procedure. Alternatively, generator 608 may comprise means for transmitting a signal to an external display. In one embodiment, generator 608 may be operable to communicate with one or more devices, for example with one or more probes 100 and/or one or more source of cooling, for example pumps 610. Such communication may be unidirectional or bidirectional depending on the devices used and the procedure performed. An example of an RF generator that may be used as part of a system of the present invention is the Pain Management Generator (PMG) of Baylis Medical Company Inc. (Montreal, QC, Canada). Further details regarding embodiments of energy sources are disclosed in U.S. patent application Ser. No. 11/105,527 (filed on Apr. 14, 2005) and Ser. No. 10/122,413 (filed on Apr. 16, 2002), both of which are previously incorporated herein by reference.

As an example of communication between generator 608 and other devices in a system of the present invention, generator 608 may receive temperature measurements from one or more temperature sensing devices 112. Based on the temperature measurements, generator 608 may perform some action, such as modulating the power that is sent to the probe(s). For example, power to the probe(s) could be increased when a temperature measurement is low or decreased when a measurement is high, relative to a predefined threshold level. If more than one probe is used, the generator may be operable to independently control the power sent to each probe depending on the individual temperature measurements received from the temperature sensing devices associated with each probe. In some cases, generator 608 may terminate power to one or more probe(s) 100. Thus, in some embodiments, generator 608 may receive a signal (e.g. temperature measurement) from one or more probe(s), determine the appropriate action, and send a signal (e.g. decreased or increased power) back to one or more probe(s).

Alternatively, if one or more cooling means, i.e. sources of cooling, comprises one or more pumps 610, for example peristaltic pumps, the one or more pumps 610 may communicate a fluid flow rate to generator 608 and may receive communications from generator 608 instructing pump(s) 610 to modulate this flow rate depending, for example, on temperature measurements received by generator 608. In some embodiments, the pump(s) 610 may respond to generator 608 by changing the flow rate or by turning off for a period of time. The pumps may be turned off in order to allow the temperature of the tissue surrounding probe 100 to reach equilibrium, thereby allowing a more precise determination of the surrounding tissue temperature to be made. In addition, when using more than one probe 100, in embodiments where the generator does not control each of the probes independently, the average temperature or a maximum temperature in the temperature sensing elements associated with probe(s) 100 may be used to control the cooling means.

As mentioned hereinabove, in some embodiments, one or more peristaltic pumps 610 may be used to supply a cooling fluid to and return a cooling fluid from probe(s) 100. In other embodiments, other types of pumps may be used. Examples include, but are not limited to, a centrifugal pump or a piston pump. As mentioned above with respect to temperature control, controlling the delivery of a cooling fluid, or other cooling means, may be performed for each probe independently or the cooling may be controlled based on an average temperature measurement or a measurement recorded from one probe, for example. Further details regarding the cooling source are provided in U.S. patent application Ser. No. 11/105,527 (filed on Apr. 14, 2005) and Ser. No. 10/864,410 (filed on Dec. 10, 2005).

In some embodiments, systems of the present invention may comprise one probe; in other embodiments, systems of the present invention may comprise a plurality of, for example two, probes. The system may be operated, for example, in a monopolar mode, a bipolar mode, or a multiphasic/multi-polar mode. When operated in a monopolar mode, any number of probes may be used, and the system may further comprise a dispersive return electrode. The dispersive return electrode may be, for example, a grounding pad for attaching to the patient's skin, or may be a substantially large electrode that is integral with probe 100. When the system is operated in a bipolar mode, any number of probes, for example 2 probes, may be used, and current may travel between the probes. Alternatively, when one probe is used, current may travel between an conductive portion 118 and a second electrically conductive and exposed portion on probe 100. For example, probe 100 may comprise a second electrically conductive and exposed portion in the form of a ring that is disposed around probe 100 at a location proximal to conductive portion 118. Conductive portion 118 and the second electrically conductive and exposed portion may be electrically isolated from each other, and probe 100 may comprise means for operatively connecting the second electrically conductive and exposed portion to a source of energy which is at a different electrical potential than electrode 118, or to a circuit ground.

The operation of the system may be manually controlled by a user, or may be automatically controlled based on certain parameters, for example, based on a measurement of a property of a component of is the system itself or of a property of the tissue being treated. When more than one probe is used, means of controlling the operation of the system may be configured to independently control each probe such that, for example, current flow to any of the probes may be independently adjustable. In addition, a flow of cooling may be controlled independently to each probe. Thus, if one probe is found to be at a higher temperature relative to another probe or probes, flow of cooling to that probe may be increased and/or current flow to that probe may be decreased. Similarly, if one probe is found to be at a lower temperature relative to another probe or probes, flow of cooling to that probe may be decreased and/or current flow to the probe may be increased. In embodiments of a system having automatic control, the system may comprise a controller operable to control one or more devices based on specified criteria. Further details regarding automatic or manual control of the system are provided in U.S. patent application Ser. No. 11/105,527 (filed on Apr. 14, 2005).

In general, embodiments of a method of the present invention involve using a treatment device, for example a probe, in a particular region of a patient's body to form a lesion of sufficient size and suitable geometry to effectively treat the target tissue. For example, in one broad aspect, a method is provided for creating a lesion at a target site within a body of a human or animal using an electrosurgical device having a longitudinal axis. The method may comprise the steps of: inserting the electrosurgical device into the body such that the electrosurgical device is generally upstanding relative to the target site; and delivering energy from an energy source solely through a distal face 107 of the electrosurgical device to the target site for creating the lesion at the target site.

The desired size and geometry of the lesion may depend on the specific anatomy and tissue being targeted and may be affected by several parameters as described herein, including but not limited to the geometry of the treatment device and the amount of cooling delivered to the treatment device. Thus, in accordance with one aspect of the present invention, steps are provided for creating a lesion with desired characteristics during the course of an electrosurgical procedure. The lesion may function to inhibit neural activity, for example nociception. Alternatively, in some embodiments, the lesion may have other effects, for example the shrinkage of collagen. Method embodiments of the present invention generally comprise one or more of the steps of: determining a desired lesion shape, size, and location; selecting an electrosurgical instrument or device, for example a probe, and energy delivery parameters, for example voltage, based on the desired lesion shape, size, and location; inserting the electrosurgical instrument or device into a patient's body; positioning the electrosurgical instrument or device at a target site; delivering energy, for example radiofrequency current, through the electrosurgical instrument or device to the target site to form a lesion; and applying cooling to the electrosurgical instrument or device. As will presently be discussed, embodiments of the method aspect of the present invention may be useful, for example, to allow for more straightforward device placement during electrosurgical procedures than is presently possible.

In one embodiment of the method aspect of the present invention, the step of inserting an electrosurgical instrument or device comprises inserting a probe percutaneously into a patient's body, and the step of positioning an electrosurgical instrument or device comprises advancing the electrosurgical instrument or device until the active electrode is at or in the vicinity of a target treatment site. The step of inserting a probe may optionally be preceded by one or more additional steps including, for example, inserting an introducer apparatus into the body in the vicinity of the target treatment site, measuring one or more properties of a device or of tissue at or near the target treatment site, inserting or removing material at or near the target treatment site, and performing another treatment procedure at or near the target treatment site.

As described above, in some embodiments, the probe may be used in conjunction with an introducer apparatus, which may comprise a cannula and an obturator, for example. In use, the obturator may be initially disposed within a lumen of the cannula to facilitate insertion of the introducer apparatus to the target treatment site. Once the introducer apparatus has been properly positioned, the obturator may be removed and replaced within the cannula lumen by the probe. In some embodiments, as described further herein below, the obturator may be operable to measure the impedance of tissue as the introducer apparatus is inserted into the patient's body which may assist in positioning the introducer apparatus at the target site. Alternatively or in addition, the obturator may be operable to deliver stimulation energy to the target treatment site, as described below. The probe and cannula may be structured such that when the probe is fully disposed within the cannula, the distal end of the probe may be aligned with the distal end of the cannula. In other embodiments, the probe and cannula may be structured such that when the probe is fully disposed within the cannula, the distal end of the probe protrudes or extends from the distal end of the cannula. For example, as described above, if the cannula comprises an electrically conductive elongate member covered by electrically insulating material, with a distal portion that is electrically conductive and exposed, then the probe may be operable to deliver energy from an energy source to the conductive distal portion of the cannula. This delivery of energy may be facilitated by physical contact between the tip of the probe and the inner surface of the cannula. In such an embodiment, the probe tip may be aligned with the distal end of the cannula and the length of the exposed conductive portion of the cannula will affect characteristics of the resulting lesion, as has been described above with reference to FIG. 5. Alternatively, in some embodiments, the cannula may comprise an electrically insulated elongate member not having a conductive and exposed distal portion. In such embodiments, the distal end of the probe may protrude or extend from the distal end of the cannula and the distance that the probe tip extends may be altered by advancing or retracting the probe. The distance that the probe tip extends from the cannula will affect the formation of the lesion, as described above.

During the steps of inserting and positioning the probe, the probe may be inserted and positioned such that the distal end of the probe, comprising the active electrode, is the portion of the probe that is closest to the treatment site. If the treatment site comprises a surface, for example, the probe may be inserted and positioned substantially perpendicular or generally upstanding to the surface, for example at an angle between about 80° and about 100° relative to the surface. In other embodiments, the probe may be positioned at an angle between about 45° and 135° or, in alternate embodiments, between about 60° and 120°. The probe may be inserted and positioned such that the distal end of the probe is directly adjacent to, or in contact with the target treatment site, or may be inserted and positioned such that the distal end of the probe is proximal to the target site. For example, in one embodiment, a probe may be inserted and positioned using what may be described as a 'perpendicular' or 'gun-barrel' approach. In this embodiment, the probe may be directed to the target site such that its longitudinal axis is substantially perpendicular or generally upstanding to the line or plane formed by the target tissue or site. For example, if the target tissue is a nerve, the probe may be positioned such that the probe is substantially perpendicular or generally upstanding relative to the nerve. If the target tissue comprises more than one neural structure, such as a nerve or nerve branch, the probe may be inserted and positioned such that it is substantially perpendicular or generally upstanding to a plane containing the neural structures. As will be described in more detail hereinbelow, embodiments of the present invention may allow for the creation of a lesion that is located primarily distally with respect to the distal end of a probe, thus allowing a probe that has been inserted substantially perpendicularly or generally upstanding relative to a target site to effectively treat the target site by delivering energy to form a lesion distal to the probe.

In alternate embodiments, the probe may be inserted at various angles to the target treatment site, depending on the procedure being performed and the anatomical structures involved. For example, in some embodiments, the probe may be inserted such that it is substantially parallel to a target nerve, for example at an angle of between about 0° and about 20°. In other embodiments, the probe may be inserted such that it is at an angle of between about 20° to about 70° to the target site. In general, embodiments of the present invention allow for various angles of approach by providing an apparatus and method of use thereof for creating a lesion of variable size and at various locations relative to the apparatus.

The step of inserting and positioning a probe may involve the insertion of a single probe to a location in the vicinity of a single target treatment site, the insertion of multiple probes in the vicinity of a single target treatment site, or the insertion of multiple probes to multiple locations in the vicinity of multiple target treatment sites. The probe or probes may be configured to deliver energy in a monopolar, bipolar or multi-polar configuration. If the probe or probes are configured to deliver energy in a monopolar configuration, the method of the current invention may also comprise a step of placing a reference electrode, such as a grounding pad, at another location on or in the body. The steps of inserting and positioning a probe may optionally be followed by any number of steps, for example prior to the commencement of the step of delivering energy including, but not limited to, one or more of: measuring one or more properties of a device or of tissue at or near the target treatment site; applying a stimulation signal to a tissue (for example, neural tissue) at or near the target treatment site; measuring the reaction to stimulation (for example, the somato-sensory evoked potential, or SSEP) of a tissue (for example, muscular or neural tissue) in response to the application of a stimulation signal at or near the target treatment site; inserting or removing material at or near the target treatment site; and performing another treatment procedure at or near the target treatment site. Further details regarding these steps may be found in U.S. patent application Ser. No. 11/105,527 (filed on Apr. 14, 2005), Ser. No. 11/280,604 (filed on Nov. 15, 2005), Ser. No. 11/356,706 (filed on Feb. 17, 2006), Ser. No. 11/381,783 (filed on May 5, 2006), and Ser. No. 11/368,509 (filed on Mar. 7, 2006). Following the performance of one or more of the above optional steps, one or more probes may be reinserted, moved, or otherwise repositioned and any optional steps may then be repeated.

In some embodiments, wherein the method comprises the step of measuring the reaction to stimulation, the stimulation energy may be delivered to a location that lies distal to the probe. For example, in embodiments using a cooled probe wherein a lesion is to be formed distal to the distal end of the probe, it may be desired to stimulate the region distal to the distal end of the probe. This can be accomplished by inserting an introducer comprising a stylet that is substantially longer than a cannula. If the stylet extends from the distal end of the cannula to a location where a lesion is expected to form, stimulation energy may be delivered through the stylet, such that the tissue surrounding the distal end of the stylet is stimulated.

The step of delivering energy to the target treatment site, for example to create a lesion at the target treatment site, may involve the creation of a lesion of a desired shape and at a desired location relative to the probe. As mentioned hereinabove, lesion shape and location may be affected by the length of the exposed distal end of the probe. The less of the probe that is exposed, the more distally, relative to the probe, the lesion will form. In addition, the shape of the lesion will be generally more spherical if less of the tip is exposed. For example, if the exposed length of the distal end is limited substantially to the distal-most hemisphere, i.e. the face, of the tip, then a substantially spherical lesion may form primarily distally with respect to the probe. Such a probe may be positioned such that the active electrode of the probe lies substantially proximal from the target site, for example a nerve. Energy may then be delivered to the probe such that a lesion may form substantially distal to the active electrode of the probe. Conversely, if more of the tip is exposed, then the lesion will appear more oblate and may form more radially (i.e. perpendicular to the longitudinal axis of the probe) around the distal end and the component of the lesion distal to the distal end will decrease.

The type, parameters, and properties of the energy delivered to the probe may vary depending on the application, and the invention is not limited in this regard. The energy may be one of various types of energy, for example electromagnetic, microwave, or thermal. In some embodiments, radiofrequency electrical current having a frequency of between about 10 kHz and about 1000 kHz, at a power of about 50 W, may be delivered to the probe.

In some embodiments of the method of the present invention, the step of delivering energy to the tissue may be preceded by, and/or done coincidently with, a step of applying cooling. Cooling may be used to reduce the temperature of the tissue in the vicinity of the site of energy delivery, allowing more energy to be applied without causing an increase to an unsafe temperature in local tissue. The application of more energy allows regions of tissue further away from the electrode(s) to reach a temperature at which a lesion can form, thus increasing the maximum size/volume of the lesion. Furthermore, depending on the structure of the probe, cooling may allow for a lesion to form at a position that is substantially distal to and, in some embodiments, spaced from the probe. Further details regarding cooled probes are disclosed in U.S. Provisional Patent Application 60/743,511 (Filed on Mar. 16, 2006), and 60/595,559 (Filed on Jul. 14, 2005), both of which are incorporated herein by reference. Thus, cooling an electrosurgical probe may change the size, shape, and location of formation of a lesion. As noted above, the theory described herein regarding tissue heating and lesion formation is not intended to limit the present invention in any way.

Figure 7:
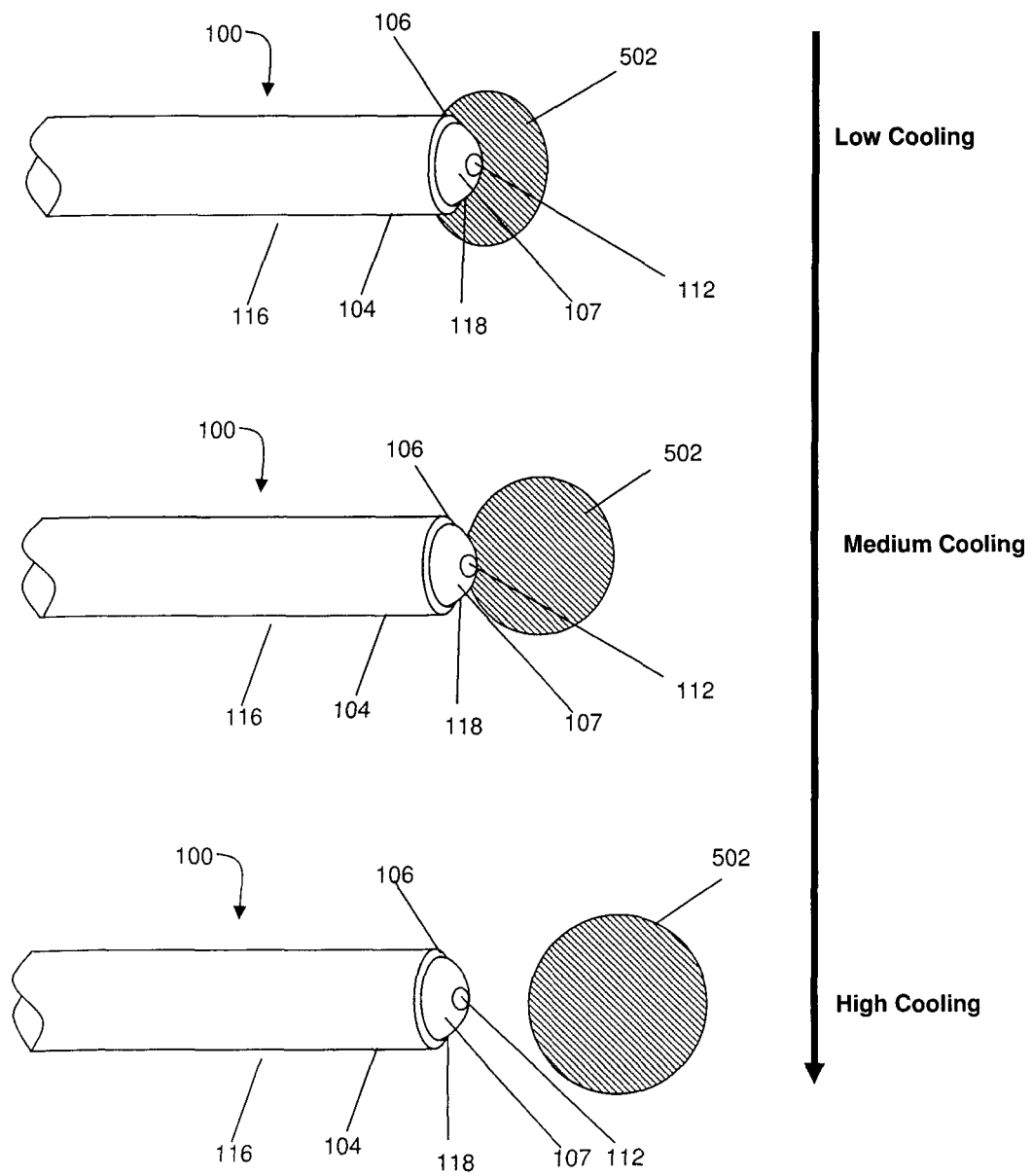
FIG. 7 is a comparative partial perspective view showing the distal region of an embodiment of a probe of the present invention and examples of lesions that may be formed with various degrees of cooling.

In one embodiment, a step of applying cooling may be used to facilitate the creation of a lesion that is distal to probe 100 and which is spaced from probe 100, as shown in FIG. 7. As long as a sufficient amount of cooling is applied to maintain the temperature of the tissue surrounding the distal end of probe 100 below the temperature at which a lesion will form (approximately 42° C.), a sufficient amount of power may be supplied from an energy source to create a lesion at some distance away from, for example distal to, probe 100. The distance of the lesion from the probe may depend on the amount of cooling delivered. In this context, low cooling refers to cooling with either a higher temperature fluid and/or at a slower volumetric flow rate, whereas higher cooling refers to cooling with either a lower temperature fluid and/or at a higher flow rate. For example, as shown in FIG. 7, if a relatively low amount of cooling is supplied, the lesion may be relatively close to the probe. If a higher amount of cooling is supplied, the lesion may form further away from the probe. This application of the method of the present invention may be used in cases where the target treatment site is not directly accessible by the probe, for example where the target site comprises, lies within, or is disrupted by a crevice, fissure, or other uneven surface feature. As discussed previously, the application of cooling can be used to allow the creation of a lesion in a region of tissue further from the probe than might be possible without cooling. Cooling can thus be used to control the position of a lesion more precisely, with increased cooling allowing the creation of a lesion further from the probe.

Additionally, cooling may be modulated during energy delivery (and in some cases, accompanied by modulation of energy delivery) as follows: energy may be delivered initially in conjunction with cooling so that a lesion begins to form at some distance distally spaced apart from the probe; cooling may then be reduced, causing the lesion to extend at least partially in the direction of the probe. Thus, a further aspect of some embodiments of the method aspect of the present invention involves the control of cooling parameters in order to create a lesion at a desired location relative to the probe. For example, an 18 AWG probe having an exposed distal tip about 1.5 mm to about 2 mm in length and being cooled by a cooling fluid having a temperature of less than 30 degrees Celsius at a rate of at least 10 mL/minute, will form a lesion about 1.5 mm distal to the probe tip. As the cooling is decreased, for example by lowering the fluid flow rate, the lesion will form closer to the probe tip. As has been mentioned with respect to adjusting the exposed length of the distal end, cooling parameters may be adjusted before, during or after energy delivery.

Thus, embodiments of a method aspect of the present invention provide for creating a lesion having a desired shape, size and location based on one or more factors, including, but not limited to, probe geometry and degree of cooling. The desired lesion parameters may be determined by a user in advance of a treatment procedure based, in some embodiments, on the specific tissue being targeted, as well as individual patient anatomy. For example, in procedures wherein the target site for formation of a lesion is located within a fissure, groove, or rut in a bone, it may not be possible to position the probe at the target site, and thus it may be desired to position the probe 100 at a location spaced from the target site. In this case, the user may select a probe 100 wherein the electrically exposed conductive portion 118 comprises only the distal face 107 of the probe, and may select a high flow and/or low temperature of cooling fluid. Such a configuration may allow for the formation of a lesion distal to the probe tip 118, thus allowing the probe tip 118 to be located at some distance from the target site. If the probe 100 is positioned substantially perpendicular to the target site, a lesion may form at a location distal to the distal end of the probe, i.e. within the fissure in the bone. In another example, the target site may be directly on the surface of a bone. In this case the user may select a probe 100 wherein the conductive portion 118 extends along the shaft proximally from the distal end, and may select a moderate or low amount of cooling. The user may position the distal end of the probe adjacent to the target site, for example about 0.1 to about 3 mm from the target site, or may allow the distal end of the probe 100 to touch the bone, and may orient the probe such that the longitudinal axis of the probe 100 is substantially perpendicular to the bone. In this case a lesion may form around the conductive portion of the probe 100, and between the distal end of the probe 100 and the bone. Alternatively, the aforementioned probe 100 having an electrode 118 comprising only the exposed distal face 107 may be used in this case as well. In both of these examples, a probe 100 with an adjustable insulating sheath may be used to provide an appropriately sized exposed electrode 118 to produce the desired lesion. Alternatively, as mentioned hereinabove, the position of a probe within a cannula or introducer may be altered by advancing and/or retracting the probe to provide an appropriately sized exposed electrode 118 to produce the desired lesion.

Figure 8A:
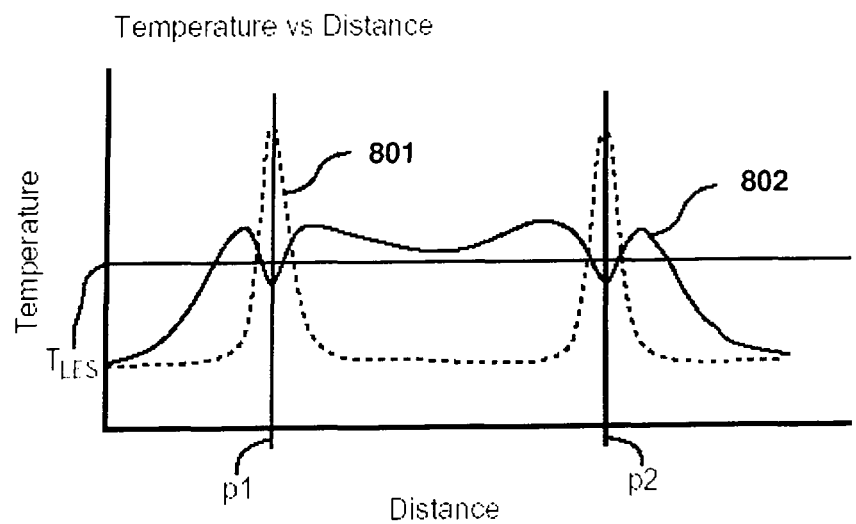
FIG. 8A is a graph of temperature in a uniform tissue vs. relative distance using an embodiment of a probe of the present invention with cooling and without cooling.
Figure 8B:
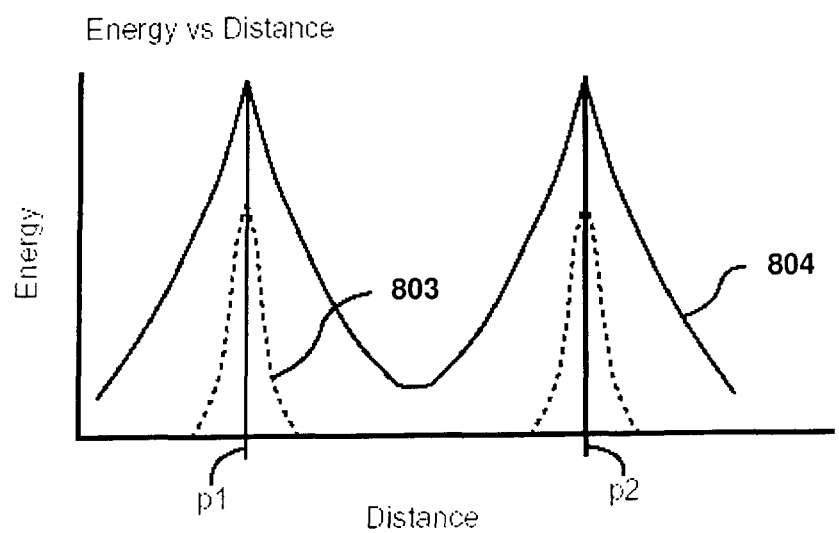
FIG. 8B is a graph of energy in a uniform tissue vs. relative distance using an embodiment of a probe of the present invention with cooling and without cooling.

In some embodiments, two cooled probes 100 in a bipolar configuration may be used, which may allow for the creation of a substantially uniform lesion between the electrodes of the two probes 100. This concept is illustrated in FIG. 8A, showing a graph of temperature vs. distance in a tissue with uniform thermal/electrical properties. The electrodes 118 of the two probes 100 are located at positions p1 and p2 on the x-axis and the temperature needed to create a lesion is noted as $T_{LES}$ on the y-axis. In FIGS. 8A and 8B, solid lines 802 and 804 represent a cooled probe assembly, while dashed lines 801 and 803 represent a non-cooled probe assembly. Without the benefits of cooling, the higher the power that is supplied to electrodes 118, the higher the temperature around electrodes 118 will be. Curve 801 shows a temperature profile, as may be typically achieved using non-cooled probes in a uniform tissue. In such a configuration it is difficult to create a lesion extending from p1 to p2 because by supplying a large amount of power to electrodes 118, the temperature at the locations p1 and p2 of the electrodes reaches very high levels. High temperatures at the electrodes may cause nearby tissue to char and possibly adhere to distal regions 104. Furthermore, raising the temperature of tissue causes the impedance of the tissue to increase and limits the penetration of current into the tissue, thereby limiting the size of the lesion that can be created. In contrast, cooled probe assemblies may be used to form a desired lesion between p1 and p2 while reducing such temperature effects. Curve 802 shows a typical temperature profile for a uniform tissue as may be seen when using two cooled probe assemblies. The temperatures at the distal end regions, p1 and p2, are reduced relative to the surrounding tissue due to the effect of the cooling. This allows for higher power to be transmitted to electrodes 118 without concern for tissue charring. In addition, because the temperature of tissue surrounding electrodes 118 is reduced, the impedance of the surrounding tissue will not increase significantly and therefore current supplied by electrodes 118 can penetrate more deeply into the tissue. As illustrated in FIG. 8A, a lesion can therefore be created between p1 and p2 using cooled probes due to the lower local temperatures at p1 and p2. Although FIG. 8A shows the temperature at p1 and p2 to be below the lesioning temperature, the cooling supplied to the cooled probes may be reduced or eliminated allowing the temperature of tissue around p1 and p2 to increase in order to complete the lesion between p1 and p2.

In some embodiments, after the creation of a lesion, the probe 100 may be repositioned, and energy may again be delivered in order to form a further lesion. For example, after the formation of a first lesion, the probe 100 may be withdrawn from the target site either partially or fully. In the case of partial withdrawal, energy may be delivered to the site at which the probe 100 has been withdrawn to, such that a further lesion is formed. In the case of full withdrawal, the probe may be re-inserted and re-positioned at a second location, and energy may be delivered to the second location to form a further lesion. The step of repositioning may be performed any number of times, to form any number of lesions, as determined by a user. In embodiments comprising a steerable probe, the probe may be repositioned without withdrawing the probe, by actuating the steering means associated with the probe.

Methods of the present invention may be used for various applications, including for the treatment of pain associated with many conditions. Examples of such conditions include, but are not limited to, Complex Regional Pain Syndrome (CRPS), Trigeminal Neuralgia, Joint Specific Peripheral Neuropathy, Facet Joint Pain, Intervertebral disc pain, Sacroiliac Joint Syndrome (SIJS) and Hypogastric or Pelvic Pain. In general, these conditions may be treated by affecting at least one target neural structure that may be associated with a patient's pain in accordance with method embodiments of the present invention. For example, in the case of trigeminal neuralgia, embodiments of the present invention may be used to form a lesion at the trigeminal nerve. Some embodiments of a method of the present invention may also be used to treat further sources of pain, as will be described in more detail hereinbelow.

In some embodiments of the present invention, the use of an introducer apparatus may not be required to insert a probe into a patient's body. For example, as is disclosed in co-pending U.S. patent application Ser. No. 11/207,707 (Filed on Aug. 22, 2005), incorporated herein by reference, an electrosurgical device or instrument, for example a probe, may be structured such that it is capable of piercing skin as well as delivering energy. The electrosurgical instrument or device may further be capable of delivering fluids to a target site. Therefore, in such embodiments, the electrosurgical device or instrument may be percutaneously inserted into the patient and directed to the target site without the use of a separate introducer apparatus.

In some embodiments, any or all of the method steps described above may be performed with the aid of imaging. For example, the step of inserting a probe may be performed under X-ray fluoroscopic guidance. In a further embodiment, the imaging may be performed in a gun-barrel manner, wherein the device is visualized along its longitudinal axis.

In some embodiments, rather than being delivered in a continuous manner, energy may be delivered in a series of amplitude or frequency modulated pulses, whereby tissue heating is inhibited by interrupting periods of energy delivery with periods in which energy is delivered at a lower voltage. In one specific embodiment, energy is delivered according to a set duty cycle of signal on time/off time, wherein the signal is 'on' less than 100% of the time, as follows: during signal 'on time' energy is delivered at a voltage that may beneficially be higher than voltages that can safely be used during continuous energy delivery (100% duty cycle) procedures; during signal 'off time', the heat generated in the vicinity of the probe may disperse throughout the tissue, raising the temperature of tissue away from the probe, while tissue in the vicinity of the probe drops; energy is again applied and the delivery is cycled through 'on time' and 'off time' until a predetermined endpoint (e.g. time or temperature) is reached or until a practitioner decides to end the treatment. The reduction in temperature of tissue in the vicinity of the probe during signal 'off time' may allow a higher voltage to be used (during 'on time'), than would tend to be used in a continuous energy delivery procedure. In this way, the pulsing of energy delivery, either between signal 'on time' and 'off time', as described above, or between a higher voltage and a lower voltage (for example, a voltage capable of generating a lesion in the tissue and a voltage not capable of generating a lesion in the tissue, given the frequency of energy being delivered), the total amount of current deposited into the tissue may be sufficient to create a larger lesion, at a further distance from the probe, than would be possible using continuous energy delivery without maintaining the tissue in the vicinity of the probe at a temperature that may cause charring.

In further embodiments, the step of cooling the probe may be performed in a pulsed or intermittent manner. This may allow for a more accurate measurement of tissue temperature by a temperature sensing device associated with the probe. For example, in embodiments wherein the probe is cooled via the internal circulation of a cooling fluid delivered by a pump, the pump may be operated in a pulsed or intermittent manner. When the pump is 'on', fluid will circulate within the probe, and the probe and surrounding tissue will be cooled; when the pump is 'off', fluid will not circulate within the probe, and heat from the tissue in the vicinity of the probe 100 may conduct back towards the probe, causing the probe to heat to a temperature that is more indicative of the temperature of the tissue in the vicinity of the probe 100. The temperature sensing device may sense this temperature, and may thus give a more accurate reading of the temperature of the tissue in the vicinity of the probe 100. When the pump returns to the 'on' position, the probe 100 will again be cooled, and the tissue adjacent the probe will return to a cooler temperature. The pulsing of the pump may coincide with pulsing of energy delivered to the probe 100, such that cooling is only supplied to the probe 100 while energy is being delivered.

In some embodiments, the amount or degree of cooling supplied to the probe 100 may be controlled actively by a user by modifying a flow-rate, or a temperature of the cooling fluid. For example, a temperature measured at the distal region of a probe may be displayed on a screen or other display means. Based on this temperature, a user may desire to increase the amount of cooling supplied to the probe 100, for example if the temperature is above a certain threshold level. The user may, in some embodiments, adjust the amount of cooling supplied by increasing the flow-rate of cooling fluid. This may be accomplished by turning a knob on a pump, for example, or by opening a valve. In other embodiments, the control of cooling may be passive and/or automatic. For example, a computer may automatically adjust a fluid flow-rate based on a temperature measured at the distal region of the probe 100. In another example, a fluid flow-rate may be fixed during the course of a treatment procedure, and may not be modified.

As has been mentioned, a system of the present invention may be used to produce a generally uniform or substantially homogeneous lesion substantially between two probes when operated in a bipolar mode. In certain cases, generally uniform or substantially homogeneous lesions may be contraindicated, such as in a case where a tissue to be treated is located closer to one active electrode than to the other. In cases where a uniform lesion may be undesirable, using two or more cooled probes in combination with a suitable feedback and control system may allow for the creation of lesions of varying size and shape. For example, preset temperature and/or power profiles that the procedure should follow may be programmed into a generator prior to commencement of a treatment procedure. These profiles may define parameters (these parameters would depend on certain tissue parameters, such as heat capacity, etc.) that should be used in order to create a lesion of a specific size and shape. These parameters may include, but are not limited to, maximum allowable temperature, ramp rate (i.e. how quickly the temperature is raised) and the rate of cooling fluid flow, for each individual probe. Based on temperature or impedance measurements performed during the procedure, various parameters, such as power or cooling, may be modulated, in order to comply with the preset profiles, resulting in a lesion with the desired dimensions. Similarly, it is to be understood that a uniform lesion can be created, using a system of the present invention, using many different pre-set temperature and/or power profiles which allow the thermal dose across the tissue to be as uniform as possible, and that the present invention is not limited in this regard.

Embodiments of the method aspect of the present invention may be useful for creating a lesion having a desired shape, size and/or location within various tissues of a human or animal. More specifically, some embodiments of the present invention may comprise treatment procedures for treating one or more target tissue sites associated with a patient's vertebral column. For example, treatment procedures may be performed at various locations external to the vertebrae, including but not limited to target sites at the cervical, thoracic, lumbar and sacral regions of the spine. In addition, treatment procedures may be performed at target sites within the vertebrae themselves, referred to as an intraosseous procedure. Furthermore, treatment procedures may be performed at target sites within one or more intervertebral discs. Although several exemplary embodiments of such procedures will be presently described, the present invention is not limited to such procedures and may be practiced at various target sites within a patient's body. In any or all of the embodiments disclosed herein, a treatment procedure may comprise a step of determining desired lesion parameters, including, but not limited to, shape, size and location, and selecting probe geometry, location and cooling in order to create the desired lesion.

One application of an embodiment of a method of the present invention is for the treatment of pain within or in the vicinity of an intervertebral disc. As is disclosed in U.S. Pat. No. 6,896,675 (filed on Mar. 5, 2002), and U.S. Pat. No. 6,562,033 (filed on Apr. 9, 2001), and U.S. patent application Ser. No. 11/128,342 (filed on May 13, 2005), Ser. No. 11/105,527 (filed on Apr. 14, 2005), Ser. No. 11/105,490 (filed on Apr. 14, 2005), and Ser. No. 11/105,524 (filed on Apr. 14, 2005), all of which are incorporated herein by reference, RF energy may be delivered through a cooled probe to an intervertebral disc of a patient in order, for example, to treat pain. Treatment of an intervertebral disc may generally comprise the steps of: inserting at least one probe into the intervertebral disc of a patient; and delivering energy through the probe(s) to the tissue of the intervertebral disc. As described above, the at least one probe may be cooled and the degree of cooling may affect the size, shape and/or location of a lesion formed within the disc.

Figure 9:
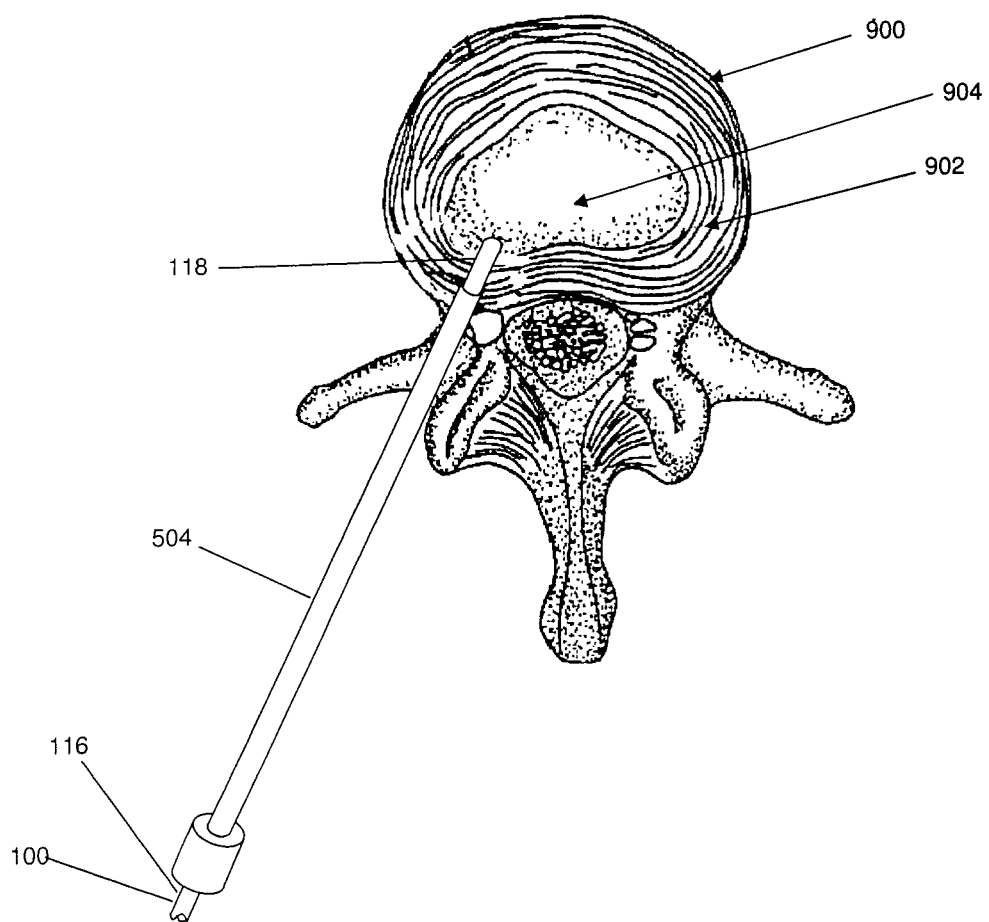
FIG. 9 is a top view of an embodiment of a probe of the present invention positioned within an intervertebral disc of a patient.

Referring to FIG. 9, the step of inserting at least one probe into an intervertebral disc 900 may proceed generally as follows (further details are provided in the aforementioned references): With a patient lying on a radiolucent table, fluoroscopic guidance may be used to insert at least one probe towards the posterior of an intervertebral disc. As mentioned above, the step of insertion may comprise the use of an introducer apparatus, for example comprising an obturator/stylet disposed within a cannula. One method of accessing the disc is the extrapedicular approach, in which the introducer passes just lateral to the pedicle, but other approaches may be used. In some embodiments, the introducer apparatus may be advanced until the distal end of the stylet penetrates the annulus fibrosis 902 and enters the nucleus pulposus 904. In other embodiments, the introducer apparatus may be advanced until the distal end of the stylet is within the annulus fibrosis 902. In further embodiments, the introducer apparatus may be advanced until the distal end of the stylet is proximal to, but not within, annulus fibrosis 902. In some particular embodiments, the stylet may be electrically connected to the generator such that the stylet forms part of an impedance monitoring circuit, as described above. In such embodiments, monitoring the impedance may assist in positioning the introducer apparatus at a desired location, since different tissues may have different impedances. When the introducer apparatus has been positioned, the stylet may be removed from the cannula. In some embodiments, a second introducer apparatus may then be placed contralateral to the first introducer in the same manner, and the stylet may be removed. After removal of the stylet(s), the probe(s) may be inserted into the introducer(s), placing the active electrodes in the disc such that the distance between active electrodes is, for example, about 1 mm to about 55 mm.

A method embodiment of the present invention may also be used to treat intraosseous target sites, i.e. target sites within a bony structure. Such procedures can be used to, for example, treat a tumor in the bony structure or lesion a neural structure within the bone. In an intraosseous procedure, one or more introducers may generally be used to gain access to the bone to be treated, for example, a vertebra of a spinal column. In such embodiments, the introducers may comprise a drill or other means for accessing the bone. Alternatively or in addition, a hammer or a reamer may be used to access an intraosseous site. As is the case with procedures related to intervertebral discs, one or more probes may be inserted at a site or sites within a bone and energy may be delivered to active electrodes located at the distal regions of the probes. Energy may be delivered in a bipolar mode, or in a monopolar mode. Furthermore, as mentioned above, one or more of the probes may be cooled to allow for the formation of a lesion having a desired size, shape and location.

Another application of embodiments of the apparatus and method of the present invention is for the treatment of pain emanating from a patient's neck, i.e. the cervical region of the spine, as is disclosed in U.S. Provisional Patent Application 60/743,511 (filed on Mar. 16, 2006), incorporated herein by reference.

Figure 10:
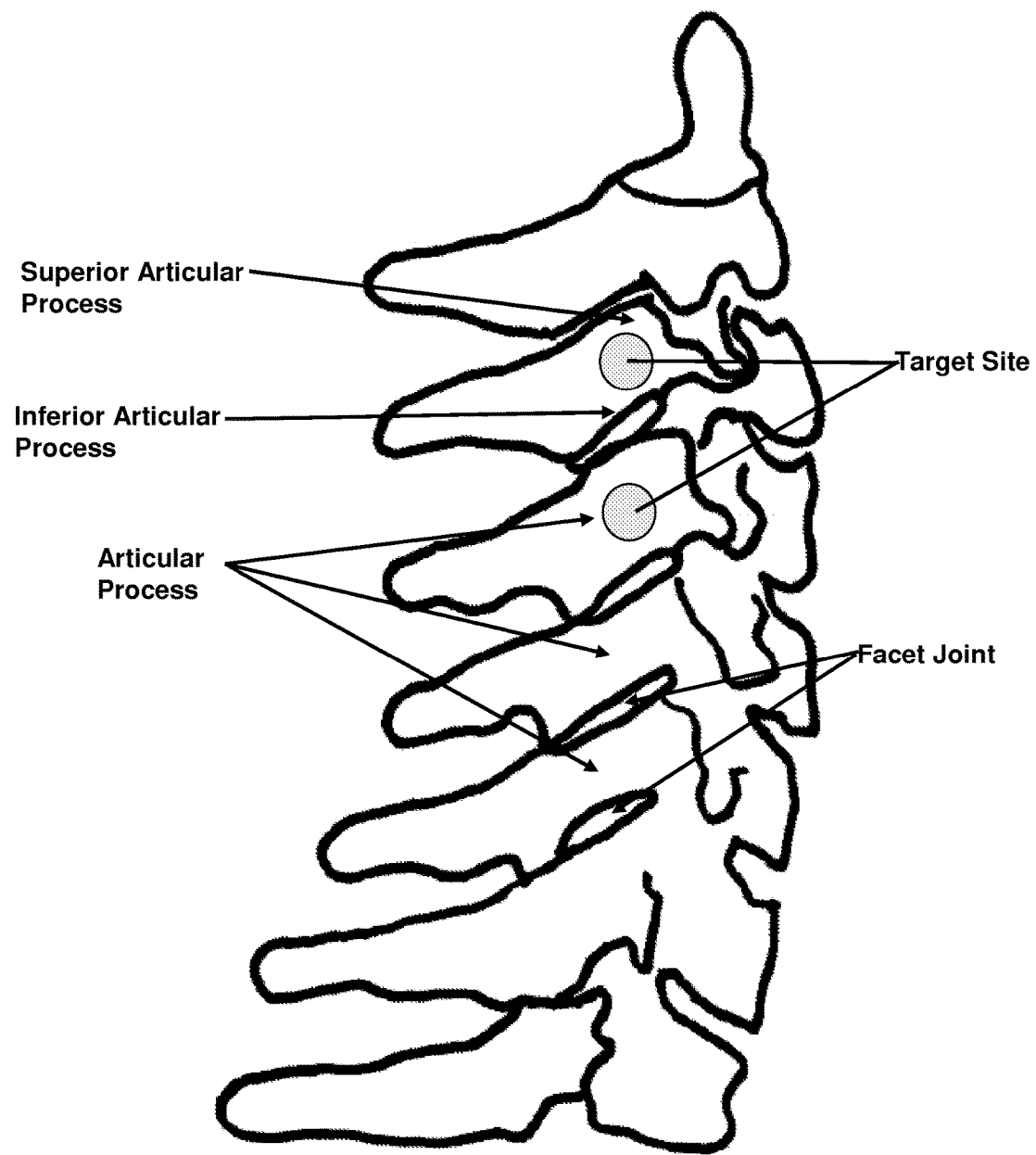
FIG. 10 is a view of the cervical vertebrae of a patient's spine, showing target sites for facet denervation.

Referring now to FIG. 10, a lateral view of the cervical region of the spine is shown. The cervical region of the spine generally comprises seven cervical vertebrae and their associated zygapophyseal, or facet, joints. Nerves innervating the facet joints are thought to be responsible for certain types of neck/cervical pain. The cervical facet joints are paired, synovial joints found along the back of the cervical vertebral column at intervertebral levels C2-3 to C7-T1. The cervical facet joints are planar joints formed between the inferior articular process of one vertebra and the superior articular process of the adjacent vertebra. Each articular process bears a circular or ovoid facet that is covered by articular cartilage, and each joint is enclosed by a fibrous joint capsule lined by a synovial membrane. The cervical facet joints are innervated by articular branches derived from the medial branches of the cervical dorsal rami. The medial branches of the typical cervical dorsal rami curve medially and posteriorly as they exit the intervertebral foramen, hugging the articular pillars. Articular branches arise as the nerve approaches the posterior aspect of the articular pillar. An ascending branch innervates the facet joint above, and a descending branch innervates the joint below.

A method of treating cervical/neck pain in accordance with one embodiment of the present invention will be presently described. The description will reference the anatomy of the facet nerve of the fourth cervical vertebra; however persons of skill in the art will recognize that the method may be used to treat other nerves of other cervical vertebrae as well, for example the third occipital nerve of the third cervical vertebra. Variations of the described method may be required in order to accommodate anatomical differences of other cervical vertebrae. In some embodiments, the target site for treating cervical/neck pain may comprise the nerves innervating the facet joint. As described hereinabove, these nerves may be located substantially adjacent to the articular pillar of the cervical vertebra. Thus the target site for energy delivery may be the region located slightly cephalad to the centroid of the articular pillar, as shown in FIG. 10.

Figure 11A:
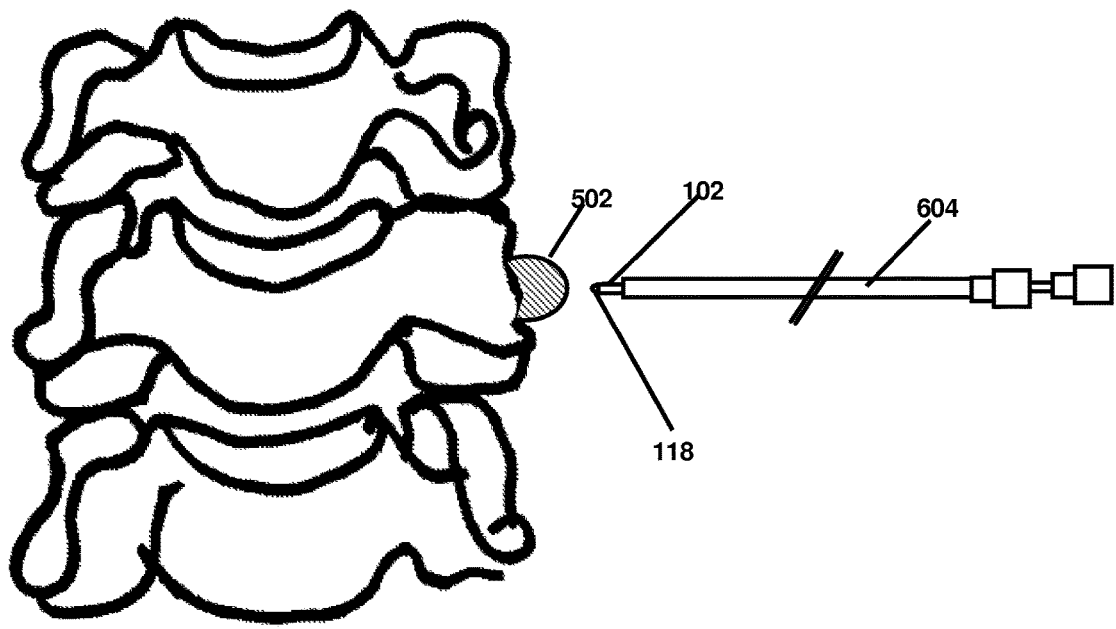
FIGS. 11A and 11B illustrate various positions of a probe with respect to the C3-C5 region of the cervical vertebrae in accordance with embodiments of the present invention.
Figure 11B:
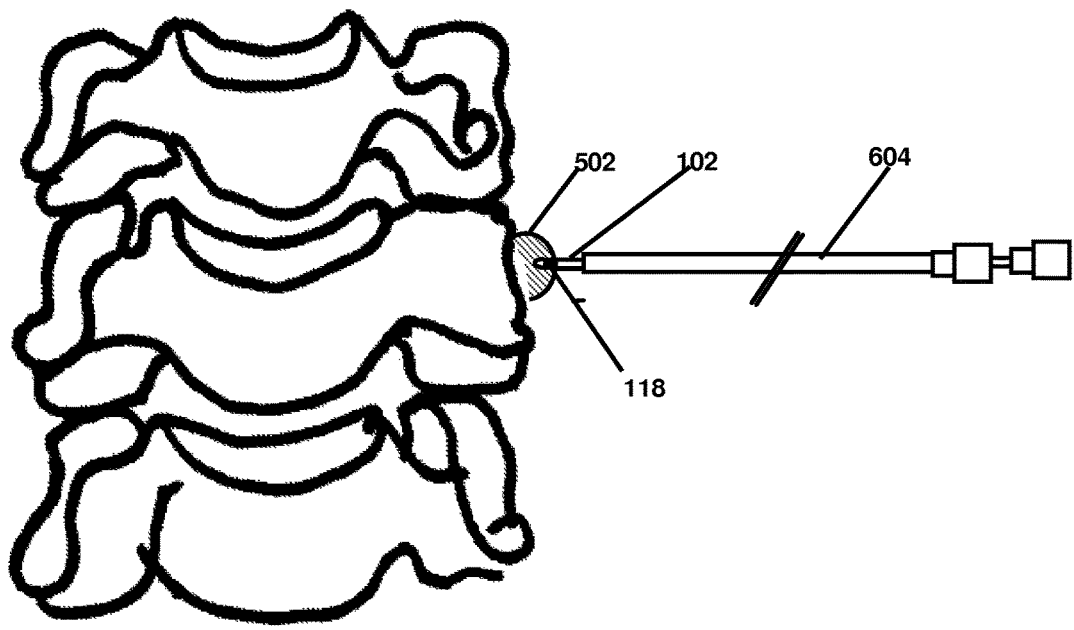

In one specific embodiment, the patient may be placed in the prone position in preparation for the treatment procedure. The user may optionally administer various treatments, such as anesthetics or antibiotics, for example. The user may insert at least one probe, such as probe 100 described hereinabove, percutaneously towards the target site. The step of inserting at least one probe may comprise the use of an introducer apparatus, as described herein above. Such an apparatus may be an introducer apparatus comprising cannula 604 and obturator 606. The user may insert the introducer apparatus percutaneously into the patient via a lateral approach, such that the longitudinal axis of the cannula is substantially perpendicular or generally upstanding, for example at an angle of about 80° to about 100°, relative to the target site, i.e. the centroid of the articular pillar. In other words, the longitudinal axis of the cannula may be substantially perpendicular or generally upstanding to the anterior-posterior (AP) axis of the body, as shown in FIGS. 11A-B, which show AP views of a portion of the cervical spine. In other embodiments, the probe may be at other angles relative to the AP axis of the body, for example between about 45° and about 135°. In yet further embodiments, the probe may be substantially parallel to the AP axis of the body. The insertion step may be facilitated with the use of fluoroscopic imaging techniques. The user may continue the insertion until a distal end of the introducer apparatus contacts the bony surface of the articular pillar, or may stop the insertion when the distal end lies some distance, for example about 2 to about 4 millimeters, proximal from the bony surface. In other embodiments, the user may contact the bony surface of the articular pillar with the tip of the introducer, and may then retract the introducer apparatus such that the distal end lies some distance proximal from the surface, as has been described. Thus, depending on the configuration and positioning of the probe and/or introducer apparatus, the distal end of the probe may be in contact with the surface of the articular pillar, or may be located some distance away from the bone. The position of the probe may be pre-determined based on the desired lesion size, shape and location, as mentioned above. The position of the probe may be verified using a variety of techniques, for example by using fluoroscopic imaging. In some embodiments, the user may use depth stoppers to aid in the marking and/or maintaining the position of the introducer apparatus within the patient's body.

When the introducer apparatus has been positioned, the user may withdraw the obturator/stylet from the cannula, leaving the cannula in place. Depending on the positioning of the introducer apparatus, the distal end of the cannula may now be touching the bone, or may be some distance proximal from the bony surface, for example about 3 mm away from the bone. The user may then insert a probe into the lumen of the cannula. The probe may be operatively connected to a source of cooling fluid, for example pumps 610, and may further be operatively connected to a source of energy, such as generator 608, in order to deliver energy to the target site.

As described above, depending on the configuration and positioning of the probe, as well as the degree of cooling, the lesion formed at the target site may be of a variety of shapes and sizes, as described hereinabove. For example, as shown in FIG. 11A, the conductive portion 118 of the probe may comprise substantially the distal face 107 of the probe. Thus, if the probe is sufficiently cooled, a lesion 502 may form distal to the probe in a substantially spherical shape. In another example, as shown in FIG. 11B, the conductive portion 1118 of the probe may extend proximally along the length of the probe for a short distance, for example between about 2 mm and about 4 mm. In such an embodiment, with a sufficient amount of cooling, a lesion 502 may form around the conductive portion as well as distal to the probe. Thus, the degree of cooling, as well as the probe geometry/configuration and positioning may each affect the lesion that may be formed. Because lesions formed by this method may reach tissue that lies within grooves or other indentations within a bone, or directly on the surface of a bone, this method may be particularly useful for lesioning of the nerves of the medial branch of the dorsal ramus at the cervical region of the spine.

Figure 12:
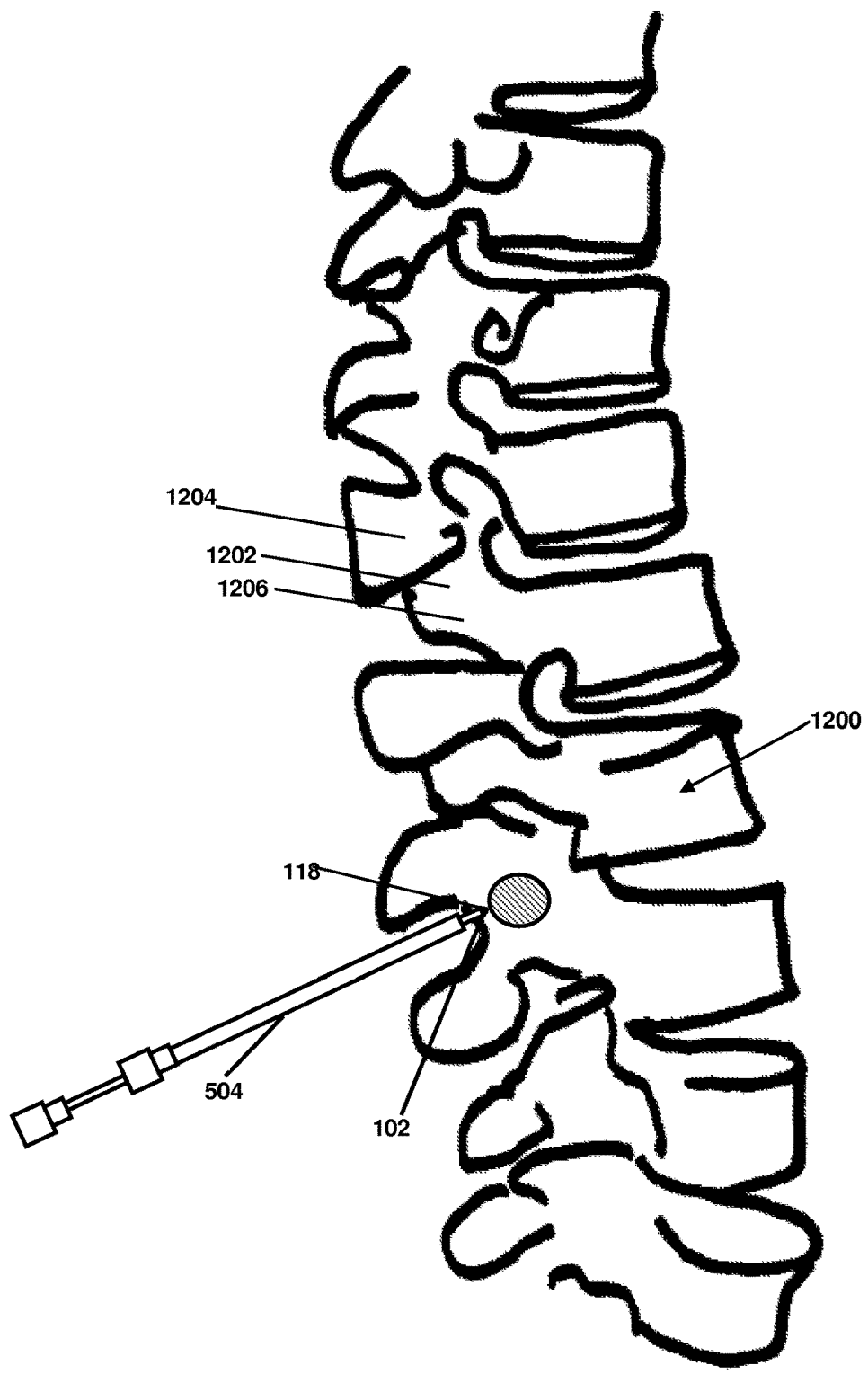
FIG. 12 illustrates a probe positioned at the lumbar region of the spine in accordance with an embodiment of the present invention.

Another application of embodiments of a method of the present invention is for the treatment of pain in the lumbar region of a patient's spine. With reference now to FIG. 12, the lumbar region generally consists of five vertebrae 1200 and their associated facet joints. The lumbar facet joints are formed by the superior 1202 and inferior 1204 articular processes of successive vertebrae. On the dorsolateral surface of each superior articular facet is a prominence known as the mammilary body or process. There is also an accessory process which arises from the dorsal surface of the transverse process 1206 near its junction with the superior articular process. The nerve supply of the lumbar facet joints is derived from the dorsal primary ramus of the nerve root. Each facet joint receives innervation from two successive medial branches of the dorsal primary ramus. At the L1-L4 levels, each dorsal ramus arises from the spinal nerve at the level of the intervertebral disc. About 5 mm from its origin, the dorsal ramus divides into a medial and lateral branch. The medial branch runs caudally and dorsally, lying against bone at the junction of the root of the transverse process with the root of the superior articular process. The medial branch runs medially and caudally just caudal to the facet joint, and becomes embedded in the fibrous tissue surrounding the joint. The medial branch gives off a branch to each of the proximal and distal facet joint. The proximal facet nerve supplies the rostra aspect of the next lower joint. The course of the medial branch of the dorsal ramus is fixed anatomically at two points: at its origin near the superior aspect of the base of the transverse process, and distally where it emerges from the canal formed by the mammillo-accessory ligament.

A method of treating lumbar pain in accordance with an embodiment of the present invention will be presently described. The description will reference the anatomy of the first lumbar vetrebra; however persons of skill in the art will recognize that the method may be used to treat other lumber vertebrae as well. Variations of the described method may be required in order to accommodate anatomical differences of other lumbar vertebrae. In some embodiments, the target site for treating lumbar pain may comprise the nerves innervating the facet joint. As described hereinabove, these nerves may be located substantially adjacent to the articular process of the lumbar vertebra. Thus the target site for energy delivery may be the dorsal surface of the transverse process just caudal to the most medial end of the superior edge of the transverse process.

In one specific embodiment, the patient may be placed in the prone position in preparation for the treatment procedure. The user may optionally administer various treatments, such as anesthetics or antibiotics, for example. The user may insert at least one probe, such as probe 100 described hereinabove, percutaneously toward the target site. In general, due to the large and controllable lesion size afforded by the structure of probe 100, probe 100 may be inserted from a number of angles and positioned at a wide variety of locations to create a lesion at the target site. The step of inserting at least one probe may comprise the use of an introducer apparatus. Such an apparatus may be an introducer apparatus comprising cannula 604 and obturator 606. The user may insert the introducer apparatus percutaneously into the patient via several different approaches. For example, in one embodiment, the introducer may be inserted in the saggital plane of the medial branch one or two levels caudal to the target site, and may be advanced in a rostral and anterior direction. In another embodiment, the introducer may be advanced from a more lateral position with oblique medial angulation. In other embodiments, the probe may be introduced at other sites, and inserted at other angles. The insertion step may be facilitated with the use of fluoroscopic imaging techniques. The user may continue the insertion until a distal end of the introducer apparatus contacts the dorsal surface of the transverse process just caudal to the most medial end of the superior edge of the transverse process, or may stop the insertion when the distal end lies some distance, for example about 2 to about 4 millimeters, proximal from the surface. In other embodiments, the user may contact the surface of the transverse process with the tip of the introducer, and may then retract the introducer apparatus such that the distal end lies some distance proximal from the surface. In some embodiments, the user may use depth stoppers to aid in the marking and/or maintaining the position of the introducer apparatus within the patient's body.

Depending on the configuration and positioning of the probe, as well the degree of cooling supplied to the probe, the lesion formed at the target site may be of a variety of shapes and sizes, as described hereinabove. For example, as shown in FIG. 12, in embodiments wherein the conductive portion 118 of the probe 100 extends proximally along the length of the probe for a small distance, for example about 2 mm to about 6 mm, for example about 4 mm, and with a sufficient amount of cooling, a lesion 502 may form around the conductive portion as well as distal to the probe. Because lesions formed by this method may reach tissue that lies within grooves or other indentations within a bone or directly on the surface of a bone, this method may be particularly useful for lesioning of the nerves of the medial branch of the dorsal ramus at the lumbar region of the spine.

Figure 13:
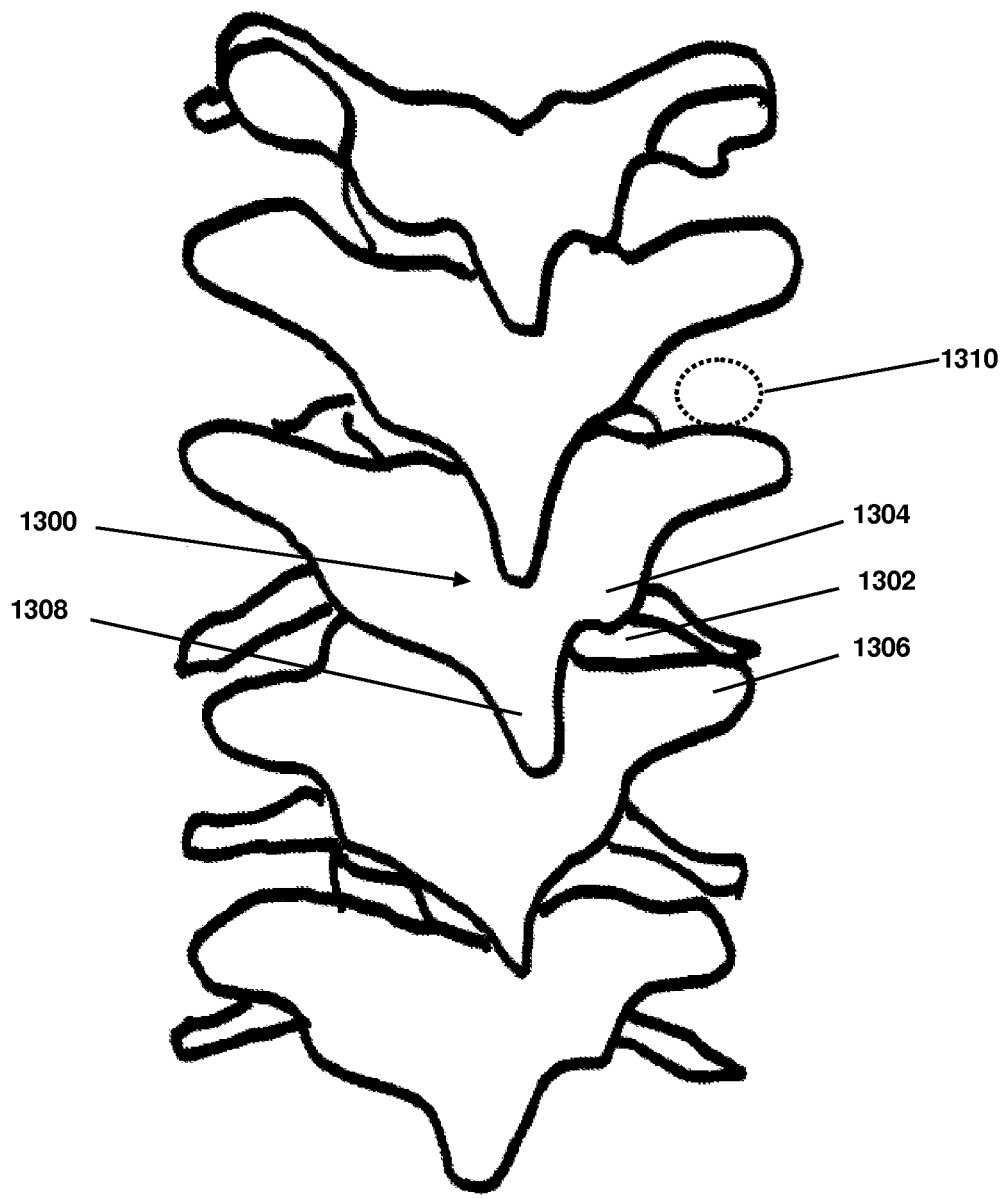
FIG. 13 is a view of the thoracic vertebrae of a patient's spine, showing a target site for energy delivery.

Referring now to FIG. 13, the vertebrae 1300 of the thoracic region are intermediate in size between those of the cervical and lumbar regions; the upper vertebrae being smaller than those in the lower part of the region. The vertebral bodies are generally as broad in the antero-posterior as in the transverse direction. At the ends of the thoracic region the vertebral bodies resemble respectively those of the cervical and lumbar vertebrae. As shown in FIG. 13, the pedicles of the thoracic vertebrae 1300 are directed backward and slightly upward. The spinous process 1308 is long and extends posterior and caudal, and ends in a tuberculated extremity. The thoracic facet joints are paired joints located between the superior 1302 and inferior 1304 articular processes of the vertebrae. The superior articular processes are thin plates of bone projecting upward from the junctions of the pedicles and laminae; their articular facets are practically flat, and are directed posteriorly and slightly lateral and upward. The inferior articular processes are fused to a considerable extent with the laminae, and project slightly beyond their lower borders; their facets are directed anteriorly and slightly medial and downward. The transverse processes 1306 arise from the arch behind the superior articular processes and pedicles; they are directed obliquely backward and lateral. The thoracic facet joints are innervated by the medial branches of the dorsal rami. The medial branches pass between consecutive transverse processes and head medially and inferiorly. They then innervate the facet joint at the level of their spinal nerve and the joint below. At T1-3 and T9-10, the medial branches cross the superior-lateral aspect of the transverse process. At T4-8, the medial branches follow a similar course, but may remain suspended within the intertransverse space. At T11-12, the medial branch has a course akin to the lumbar medial branches such that they course posteriorly along the medial aspect of the transverse process, at the root of the superior articular process.

Due to the varied course of the medial branch across the 12 thoracic levels, the lack of bony landmarks associated with the thoracic medial branch, and the anatomic differences among patients, it is often required to create several lesions in order to denervate one thoracic facet joint, as is described by Dreyfuss et al (ISIS Newsletter, December 1997, Volume 2, Number 6). Embodiments of the present invention may allow for the formation of a single large lesion for the denervation of a facet joint, for example by using cooling, thus providing a more straightforward and less invasive procedure.

A method of treating thoracic pain in accordance with an embodiment of the present invention will be presently described. The description will reference the anatomy of the first through tenth thoracic vertebrae. Variations of the described method may be required in order to accommodate anatomical differences of other thoracic vertebrae. In some embodiments, the target site for treating thoracic pain may comprise the nerves innervating the facet joint. As described hereinabove, these nerves may be located substantially laterally between two consecutive transverse processes, or substantially adjacent the superior edge of a transverse process. Thus the target site 1310 for energy delivery may be the superior lateral edge of the transverse process and the region immediately superior thereto.

In one specific embodiment, the patient may be placed in the prone position in preparation for the treatment procedure. The user may optionally administer various treatments, such as anesthetics or antibiotics, for example. The user may insert at least one probe, such as probe 100 described hereinabove, percutaneously toward the target site. In general, due to the large and controllable lesion size afforded by the structure of probe 100, probe 100 may be inserted from a number of angles and positioned at a wide variety of locations to create a lesion at the target site. The step of inserting at least one probe may comprise the use of an introducer apparatus. Such an apparatus may be an introducer apparatus comprising cannula 604 and obturator 606.

Figure 14:
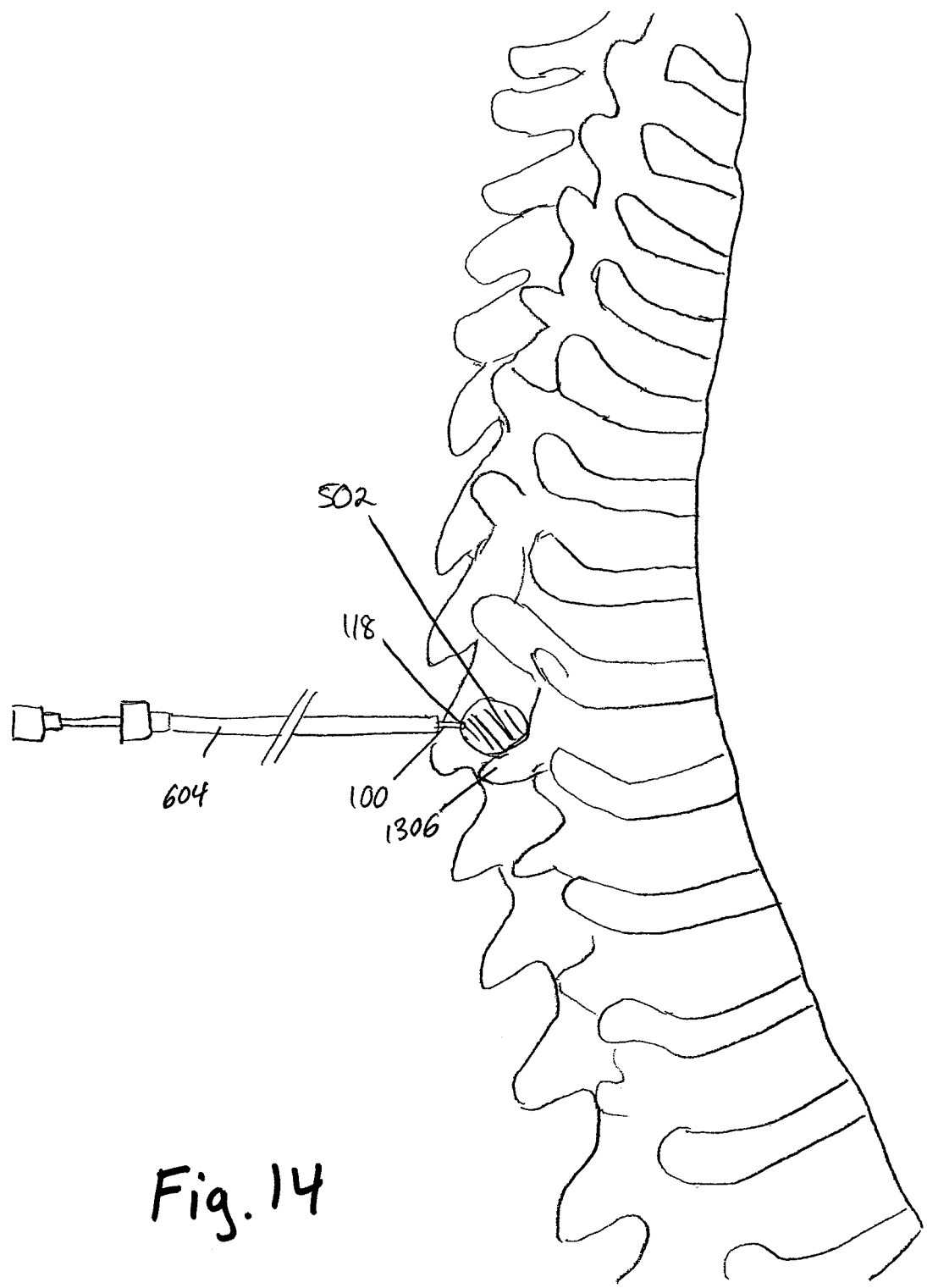
FIG. 14 illustrates a position of a probe with respect to the thoracic vertebrae in accordance with embodiments of the present invention.

The user may insert the introducer apparatus percutaneously into the patient via several different approaches. For example, as shown in FIG. 14, in one embodiment, the introducer may be inserted slightly medial to the lateral edge of transverse process 1306, and advanced in the anterior direction. In another embodiment, the introducer may be advanced from a more medial position with oblique lateral angulation. In other embodiments, the probe may be introduced at other sites, and inserted at other angles. In some embodiments, the insertion step may be facilitated with the use of fluoroscopic imaging techniques. The user may continue the insertion until a distal end of the introducer apparatus contacts transverse process 1306. The user may then "walk" the introducer apparatus in the cranial direction, until the distal end of the introducer begins to slip over the superior edge of transverse process 1306. The user may then withdraw the introducer slightly, such that the distal end of the introducer is substantially above the superior lateral edge of transverse process 1306. In some embodiments, the user may use depth stoppers to aid in the marking and/or maintaining the position of the introducer apparatus within the patient's body.

Depending, for example, on the configuration and positioning of the probe, as well as the degree of cooling supplied to the probe, the lesion formed at the target site may be of a variety of shapes and sizes, as described hereinabove. For example, as shown in FIG. 14, in embodiments wherein the conductive portion 118 of the probe 100 extends proximally along the length of the probe for a small distance, for example between about 1 mm and about 4 mm, and with a sufficient amount of cooling, for example between about 10 ml/min and about 25 ml/min, a lesion 502 may form around the conductive portion as well as distal to the probe. Because lesions formed by this method may be substantially large, for example between about 150 $mm^3$ and about 500 $mm^3$ in volume, this method may be particularly useful for lesioning of the nerves of the medial branch of the dorsal ramus at the thoracic region of the spine.

A further application of embodiments of the apparatus and method of the present invention is for the treatment of pain emanating from the Sacroiliac (SI) joint and/or the surrounding region. Some details regarding such a treatment procedure are disclosed in U.S. patent application Ser. No. 11/280,604 (filed on Nov. 15, 2005) and Ser. No. 11/356,706 (filed on Feb. 17, 2006), and U.S. Provisional Patent Application 60/627,813 (filed on Nov. 15, 2004), 60/593,839 (filed on Feb. 17, 2005), 60/594,787 (filed on May 5, 2005), 60/595,426 (filed on Jul. 4, 2005), 60/595,559 (filed on Jul. 14, 2005), 60/595,560 (filed on Jul. 14, 2005), and 60/743,663 (filed on Mar. 22, 2006), all of which are incorporated herein by reference. The SI joint 1500 is the joint between the sacrum 1502, a large bone at the base of the spine composed of five fused vertebrae, and the ilium 1504 of the pelvis. The SI joint is a relatively immobile joint, serving to absorb shock during locomotion. The structure of the SI joint and surrounding tissues varies significantly between individuals but generally comprises an articular cartilaginous surface, a ligamentous aspect and, in most cases, one or more synovial recesses. Though the specific pathways of SI joint innervation have not yet been elucidated, the nerves responsible for SI pain are thought to comprise, at least in part, nerves emanating from the dorsal sacral plexus, the network of nerves on the posterior surface of the sacrum, extending from the sacral nerves, also referred to as the posterior primary rami 1506, that exit the sacral foramina 1508 (posterior sacral foramen). The lateral branches 1510 branch out from the sacral nerves (and branch out further along the sacrum as well) and are thought to play a role in the innervation of the SI joint. The surface of the sacrum can be very uneven, inhibiting the ability of a small lesion to affect nerves running along crests of the sacrum, as well as those within the grooves or recesses in the sacral surface; furthermore, accessing the sacrum can require penetrating the sacroiliac ligaments, ligaments responsible for bearing a large proportion of the weight of the body and which, desirably, would be severed or weakened as little as possible.

Due to the anatomy of the sacrum, a straight 'gun-barrel' approach, substantially perpendicular to the plane of the sacrum or to the target site, may be desirable. However, if a target nerve to be lesioned is running through a narrow groove or fissure that is too narrow to accommodate a probe capable of creating a lesion with the desired volume, the nerve may remain distal to an inserted probe, even if the probe is in contact with the surface of the sacrum. Embodiments of the device of the present invention may be used according to embodiments of the method described above in order to create a lesion that is primarily located distal to probe 100. This may allow for a substantially perpendicular 'gun-barrel' approach and a lesion thus created may encompass the target nerve.

In some embodiments, it may be desired to treat one or more neural structures within a sacral neural crescent. The term 'sacral neural crescent' refers to an area lateral to each of the sacral foramina, through which the sacral nerves are believed to pass after exiting the foramina. On the dorsal right side of the sacrum, this window is from about 12 o'clock to about 6 o'clock in a clockwise direction, while on the dorsal left side of the sacrum the window is from about 6 o'clock to about 12 o'clock in a clockwise direction. Similar (but in the counter-clockwise direction) areas exist on the ventral side of the sacrum. The clock positions are referenced as if the foramen is viewed as a clock face, and the view is taken looking towards the sacrum. For reference, the 12 o'clock position of the clock face would be the most cephalad (towards the head) point of the foramen.

In other embodiments, methods of the present invention may be used to treat other conditions at various regions within the body, which may be external to the patient's spine. Examples of such conditions include, but are not limited to, pain-causing conditions such as Complex Regional Pain Syndrome (CRPS), Trigeminal Neuralgia, Joint Specific Peripheral Neuropathy, Facet Joint Pain, Fibrotic pain or pain due to scar tissue, and Hypogastric or Pelvic Pain. In general, these conditions may be treated by lesioning at least one target nerve that may be associated with a patient's pain in accordance with method embodiments of the present invention. For example, in the case of trigeminal neuralgia, devices and methods of the present invention may be used to form a lesion at the trigeminal nerve. In the case of CPRS, devices and methods of the present invention may be used to form a lesion at a sympathetic nerve chain.

In addition to the treatment of pain-causing conditions, methods and devices of the present invention may be used for other applications, such as cardiac ablation, for example in cases of atrial tachycardia, is removal or treatment of scar tissue, treatment of varicose veins, treatment of hyperparathyroidism, and ablation of malignancies or tumours, for example in the lung, liver, or bone. In general, these conditions may be treated by lesioning at least one target site associated with a symptom or cause of a patient's condition. For example, in the case of atrial tachycardia, devices and methods of the present invention may be used to form a lesion at the His Bundle region of the heart. In the case of hyperparathyroidism, devices and methods of the present invention may be used to form a lesion at one or more parathyroid glands.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An electrosurgical device comprising:
   an elongate member defining a lumen, the elongate member having a rounded distal face comprising one or more electrically exposed conductive portions for delivering energy distal to the distal face;
   one or more electrically insulated portions circumferentially surrounding and fixed to an outer surface of the elongate member;
   at least one of the one or more electrically insulated portions extending from a proximal region of the elongate member to the distal face and having an outer diameter adjacent the distal face that is greater than a diameter of the distal face;
   at least one tube within the lumen for at least one of delivering a fluid to or removing a fluid from a distal region of the elongate member for cooling at least a portion of the elongate member, the fluid entering and exiting the elongate member only at a proximal end of the elongate member; and
   a temperature sensor protruding from the distal face and electrically coupled to an external device via the lumen so as to measure a temperature of a material located distally to the distal face, the temperature sensor located on an external surface of the distal face and separated from the lumen via the distal face such that the fluid does not contact the temperature sensor.

2. The device of claim 1, wherein the distal face of the elongate member is flat.

3. The device of claim 1, further comprising a further internal tube for at least one of delivering a fluid to or removing a fluid from the distal region.

4. The device of claim 1, wherein the temperature sensor is selected from the group consisting of a thermocouple, a thermistor, an optical fluorescence sensor and a thermometer.

5. The device of claim 1, further comprising a sensor for measuring impedance.

6. The device of claim 1, further comprising a sensor for measuring pressure.

7. The device of claim 1, wherein the elongate member comprises an electrically conductive shaft and wherein the one or more electrically insulated portions comprise electrically insulative material disposed on the surface of the shaft.

8. The device of claim 1, wherein the elongate member comprises an electrically non-conductive shaft and wherein the elongate member further comprises at least one electrical conductor for coupling the one or more electrically exposed conductive portions to an energy source.

9. A kit comprising:
   an elongate member defining a lumen, the elongate member having a rounded distal face comprising one or more electrically exposed conductive portions for delivering energy distal to the distal face;
   one or more electrically insulated portions circumferentially surrounding and fixed to an outer surface of the elongate member;
   at least one of the one or more electrically insulated portions extending from a proximal region of the elongate member to the distal face and having an outer diameter adjacent the distal face that is greater than a diameter of the distal face,
   at least one tube within the lumen for at least one of delivering a fluid to or removing a fluid from a distal region of the elongate member for cooling at least a portion of the elongate member, the fluid entering and exiting the elongate member only at a proximal end of the elongate member;
   a temperature sensor protruding from the distal face and electrically coupled to an external device via the lumen so as to measure a temperature of a material located distally to the distal face, the temperature sensor located on an external surface of the distal face and separated from the lumen via the distal face such that the fluid does not contact the temperature sensor; and
   a cannula for facilitating insertion of the device into a patient's body.

10. The kit of claim 9, further comprising an obturator for facilitating insertion of the cannula into the patient's body.

11. A system comprising:
    an elongate member defining a lumen, the elongate member having a rounded distal face comprising one or more electrically exposed conductive portions for delivering energy distal to the distal face;
    one or more electrically insulated portions circumferentially surrounding and fixed to an outer surface of the elongate member;
    at least one of the one or more electrically insulated portions extending from a proximal region of the elongate member to the distal face and having an outer diameter adjacent the distal face that is greater than a diameter of the distal face, at least one tube within the lumen for at least one of delivering a fluid to or removing a fluid from a distal region of the elongate member for cooling at least a portion of the elongate member, the fluid entering and exiting the elongate member only at a proximal end of the elongate member;
    a temperature sensor protruding from the distal face and electrically coupled to an external device via the lumen so as to measure a temperature of a material located distally to the distal face, the temperature sensor located on an external surface of the distal face and separated from the lumen via the distal face such that the fluid does not contact the temperature sensor; and
    an energy source for delivering energy to the one or more electrically exposed conductive portions.

* * * * *